US012180469B2

(12) United States Patent
Park et al.

(10) Patent No.: US 12,180,469 B2
(45) **Date of Patent: *Dec. 31, 2024**

(54) **SURFACE EXPRESSION VECTOR FOR CONSTITUTIVE HIGH-EXPRESSION USING PROMOTER OF GALACTOSE MUTAROTASE GENE DERIVED FROM *LACTOBACILLUS CASEI*, AND USE THEREOF**

(71) Applicant: BIOLEADERS CORPORATION, Yongin-si (KR)

(72) Inventors: Young Chul Park, Seoul (KR); Dae Eun Ki, Seoul (KR); Gyeong Jun Nam, Yongin-si (KR); Se Eun Byeon, Hwaseong-si (KR); Ha Na Moon, Yongin-si (KR); Hyun Jun Kang, Goyang-si (KR); Kyung Soo Hahm, Seoul (KR)

(73) Assignee: BIOLEADERS CORPORATION, Yongin-si (KR)

( * ) Notice: Subject to any disclaimer, the term of this patent is extended or adjusted under 35 U.S.C. 154(b) by 884 days.

This patent is subject to a terminal disclaimer.

(21) Appl. No.: 17/281,743

(22) PCT Filed: Oct. 10, 2019

(86) PCT No.: PCT/KR2019/013260

§ 371 (c)(1),
(2) Date: Mar. 31, 2021

(87) PCT Pub. No.: WO2020/076078

PCT Pub. Date: Apr. 16, 2020

(65) Prior Publication Data

US 2022/0033812 A1 Feb. 3, 2022

(30) Foreign Application Priority Data

Oct. 10, 2018 (KR) ........................ 10-2018-0120546

(51) Int. Cl.

| | |
|---|---|
| ***C12N 15/11*** | (2006.01) |
| ***A61K 35/74*** | (2015.01) |
| ***A61K 39/00*** | (2006.01) |
| ***C07K 14/435*** | (2006.01) |
| ***C12N 1/20*** | (2006.01) |
| ***C12N 9/00*** | (2006.01) |
| ***C12N 9/90*** | (2006.01) |
| ***C12N 15/74*** | (2006.01) |

(52) U.S. Cl.

CPC .............. *C12N 15/11* (2013.01); *A61K 35/74* (2013.01); *A61K 39/00* (2013.01); *C07K 14/43595* (2013.01); *C12N 1/20* (2013.01); *C12N 9/90* (2013.01); *C12N 9/93* (2013.01); *C12N 15/746* (2013.01); *C12Y 501/03003* (2013.01)

(58) Field of Classification Search

CPC ........ C12N 15/11; C12N 1/20; C12N 15/746; A61K 35/74

See application file for complete search history.

(56) References Cited

U.S. PATENT DOCUMENTS

| | | | | |
|---|---|---|---|---|
| 7,553,636 B2 * | 6/2009 | Sung | C12Y 207/08005 | 435/69.7 |
| 2004/0253704 A1 * | 12/2004 | Sung | C12N 9/1051 | 435/221 |

FOREIGN PATENT DOCUMENTS

| | | | |
|---|---|---|---|
| KR | 20040032824 | 4/2004 | |
| KR | 20080086161 | 9/2008 | |
| KR | 20150092921 | 8/2015 | |
| WO | WO-03014360 A1 * | 2/2003 | C12N 15/75 |
| WO | 2008115019 | 9/2008 | |
| WO | 2010001363 | 1/2010 | |

OTHER PUBLICATIONS

Bettenbrock, K., & Alpert, C. A. (1998). The gal genes for the Leloir pathway of Lactobacillus casei 64H. Applied and environmental microbiology, 64(6), 2013-2019. (Year: 1998).*

Georgiou, George, et al. "Practical applications of engineering Gram-negative bacterial cell surfaces." Trends in biotechnology 11.1 (1993) (Year: 1993).*

Bettenbrock et al., The gal Genes for the Leloir Pathway of Lactobacillus casei 64H, Applied and Environmental Microbiology, Jun. 1998, vol. 64, No. 6, pp. 2013-2019.

(Continued)

*Primary Examiner* — Tracy Vivlemore
*Assistant Examiner* — Allison Marie Johnson
(74) *Attorney, Agent, or Firm* — CANTOR COLBURN LLP

(57) ABSTRACT

Provided is a galactose mutarotase gene promoter derived from *Lactobacillus casei* and the use thereof, and more particularly, to a *Lactobacillus casei*-derived galactose mutarotase gene promoter having the nucleotide sequence of SEQ ID NO: 1, an expression vector containing the promoter, and a microorganism transformed with the expression vector. A microorganism transformed with an expression vector containing the promoter may effectively express a target protein on the cell surface, and thus is useful as a vaccine vehicle or the like. Moreover, provided is a surface expression vector having pgsA, which is a gene encoding poly-gamma-glutamate synthetase, and a method of expressing a target protein on the microbial surface using the vector. The vector containing foreign genes inserted therein is transformed into a microorganism and allows a foreign protein is to be stably expressed on the surface of the microorganism.

14 Claims, 14 Drawing Sheets

Specification includes a Sequence Listing.

(56) References Cited

OTHER PUBLICATIONS

Goh et al., Identification of a Putative Operon Involved in Fructooligosaccharide Utilization by Lactobacillus paracasei, Applied and Environmental Microbiology, Dec. 2006, vol. 72, No. 12, pp. 7518-7530.
Sequence listing for Lactobacillus paracasei strain IIA.
Agterberg, et al., Outer membrane PhoE protein of *Escherichia coli* as a carrier for foreign antigenic determinants: immunogenicity of epitopes of foot-and-mouth disease virus, Vaccine, vol. 8, Feb. 1990, pp. 85-91.
Araujo Aires, et al., Production of Human Papillomavirus Type 16 L1 Virus-Like Particles by Recombinant Lactobacillus casei Cells, Applied and Environmental Microbiology, Jan. 2006, vol. 72, No. 1, pp. 745-752.
Charbit, et al., Presentation of Two Epitopes of The preS2 Region of Hepatitis B Virus on Live Recombinant Bacteria, The Journal of Immunology, vol. 139, No. 5, Sep. 1987, pp. 1658-1664.
De Ruyter, et al., Controlled Gene Expression Systems for Lactococcus lactis with the Food-Grade Inducer Nisin, Applied and Environmental Microbiology, Oct. 1996, vol. 62, No. 10, pp. 3662-3667.
Felici, et al., Selection of Antibody Ligands from a Large Library of Oligopeptides Expressed on a Multivalent Exposition Vector, J. Mol. Biol., 1991, vol. 222, pp. 301-310.
Fuchs, et al., Targeting Recombinant Antibodies to the Surface of *Escherichia coli*: Fusion to a Peptidoglycan Associated Lipoprotein, Bio/Technology, vol. 9, Dec. 1991, pp. 1369-1372.
Hedegaard, et al., Type 1 fimbriae of *Escherichia coli* as carriers of heterologous antigenic sequences, Gene, vol. 85, 1989, pp. 115-124.
International Search report—PCT/KR2019/013260 dated Jan. 17, 2020.
Jung, et al., Expression of carboxymethylcellulase on the surface of *Escherichia coli* using Pseudomonas syringae ice nucleation protein, Enzyme and Microbial Technology, vol. 22, Apr. 1998, pp. 348-354.
Jung, et al., Surface display of Zymomonas mobilis levansucrase by using the ice-nucleation protein of Pseudomonas syringae, Nature Biotechnology, vol. 16, Jun. 1998, pp. 576-580.
Klauser, et al., Extracellular transport of cholera toxin B subunit using Neisseria IgA protease β-domain: conformation-dependent outer membrane translocation, The EMBO Journal, 1990, vol. 9, No. 6, pp. 1991-1999.
Koivula, et al., Isolation and Characterization of *Lactococcus lactis* subsp. lactis Promoters, Applied and Environmental Microbiology, Feb. 1991, vol. 57, No. 2, pp. 333-340.
Kornacker, et al., The normally periplasmic enzyme β-lactamase is specifically and efficiently translocated through the *Escherichia coli* outer membrane when it is fused to the cell-surface enzyme pullulanase, Molecular Microbiology, 1990, vol. 4, No. 7, pp. 1101-1109.
Lee, et al., Microbial cell-surface display, Trends in Biotechnology, Jan. 2003, vol. 21, No. 1, pp. 45-52.
Lee, et al., Surface-displayed viral antigens on *Salmonella* carrier vaccine, Nature Biotechnology, Jun. 2000, vol. 18, pp. 645-648.
NCBI. GenBank accession No. FM177140.1 (Feb. 27, 2015).
Newton, et al., Immune Response to Cholera Toxin Epitope Inserted in *Salmonella flagellin*, Science, Apr. 1989, vol. 244, No. 4900, pp. 70-72.
Samuelson, et al., Cell Surface Display of Recombinant Proteins on *Staphylococcus carnosus*, Journal of Bacteriology, Mar. 1995, vol. 177, No. 6, pp. 1470-1476.
Seegers, Lactobacilli as live vaccine delivery vectors: progress and prospects, Trends in Biotechnology, Dec. 2002, vol. 20, No. 12, pp. 508-515.
Slos, et al., Isolation and Characterization of Chromosomal Promoters of *Streptococcus salivarius* subsp. thermophilus, Applied and Environmental Microbiology, May 1991, vol. 57, No. 5, pp. 1333-1339.
Steidler, et al., Biological containment of genetically modified Lactococcus lactis for intestinal delivery of human interleukin 10, Nature Biotechnology, Jul. 2003, vol. 21, No. 7, pp. 785-789.
Van Der Vossen, et al., Isolation and Characterization of *Streptococcus cremoris* Wg2-Specific Promoters, Applied and Environmental Microbiology, Oct. 1987, vol. 53, No. 10, pp. 2452-2457.

* cited by examiner

SURFACE EXPRESSION VECTOR FOR CONSTITUTIVE HIGH-EXPRESSION USING PROMOTER OF GALACTOSE MUTAROTASE GENE DERIVED FROM *LACTOBACILLUS CASEI*, AND USE THEREOF

TECHNICAL FIELD

The present invention relates to a galactose mutarotase gene promoter derived from *Lactobacillus casei*, and more particularly, to a *Lactobacillus casei*-derived galactose mutarotase gene promoter represented by SEQ ID NO: 1, an expression vector containing the promoter, and a microorganism transformed with the expression vector.

Moreover, the present invention relates to a novel vector which effectively expresses a foreign protein on the microbial surface using an outer membrane protein (pgsA) which is derived from a *Bacillus* sp. strain and involved in the synthesis of poly-gamma-glutamate. Furthermore, the present invention relates to a method of producing a protein by expressing a foreign protein on the microbial surface an outer membrane protein which is derived from a *Bacillus* sp. strain and involved in the synthesis of poly-gamma-glutamate.

BACKGROUND ART

Lactic acid bacteria, which are the most important microorganisms among food microorganisms, have acquired the GRAS (generally recognized as safe) status, and thus have been used in various foods. These lactic acid bacteria have plasmids, bacteriophages, transposons and the like, and thus make it possible to develop vectors for introducing genes into cells. Also, these lactic acid bacteria are easily transformed according to conventional methods known in the art, and are considered most suitable for edible purposes, because edible selectable marker genes have been established. In addition, lactic acid bacteria have the effects of inhibiting harmful intestinal bacteria, cleaning intestines, lowering blood cholesterol levels, increasing the nutritional value, inhibiting infection with pathogens, and alleviating liver cirrhosis, as well as an anticancer effect and the effect of boosting the immune system through macrophage activation.

In order to produce useful foreign proteins in lactic acid highly efficient bacteria, it is necessary to establish promoters (J. M. van der Vossen et al., Appl. Environ. Microbial., Vol. 53, pp 2452-2457, 1987; Teija Koivula et al., Appl. Environ. Microbial., Vol. 57, pp 333-340, 1991; Pascalle G. G. A. et al., Appl. Environ. Microbial., Vol. 62, pp 3662-3667, 1996), but studies on the genomes of lactic acid bacteria are still very insufficient. Among the genomes of lactic acid bacteria, only the genomes of *Bifidobacterium longum* NCC 2705, *Enterococcus faecalis* V583 and *Lactobacillus plantarum* WFCS 1 have been sequenced to date, and studies on the genome sequencing of a variety of lactic acid bacteria are currently in progress. In addition, as promoters isolated from lactic acid bacteria, only promoters derived from the genomes of *Streptococcus thermophilus* A054, *Lactococcus lactis* MG1614 and *Lactococcus cremoris* Wg2 (Philippe Slos et al., Appl. Environ. Microbial., Vol. 57, pp 1333-1339, 1991; Teija Koivula et al., Appl. Environ. Microbial., Vol. 57, pp 333-340, 1991; J. M. van der Vossen et al., Appl. Environ. Microbial., Vol. 53, pp 2452-2457, 1987) are known to date.

In recent years, in the United States and Europe, studies have been conducted on the development of live vaccines using lactic acid bacteria, and on carriers for delivering useful hormone drugs into the intestines and the establishment of efficient genetic resources therefor, and on the development of insertion vectors for lactic acid bacteria. In particular, since unmethylated CpG DNA, lipoteichoic acid, peptidoglycan and the like, which are contained in large amounts in lactic acid bacteria, are known to act as immune adjuvants, lactic acid bacteria have been considered highly useful as vaccine vehicles. In addition, lactic acid bacteria have a number of advantages in that they can deliver antigens to the intestines due to their resistance to bile acid and gastric acid, and thus induce mucosal immunity in the intestines (Jos F. M. K. Seegers, Trends Biotechnol., Vol. 20, pp 508-515, 2002).

However, in order to use lactic acid bacteria as vaccine vehicles, it is necessary to develop a technology of facilitating antigen-antibody reactions by presenting antigen proteins for production of disease-preventing antibodies to the inside or outside of cells. In fact, various studies revealed that lactic acid bacteria are suitable as vaccine vehicles. These studies include the confirmation of the antibody-inducing capacity of lactic acid bacteria which express the L1 protein of human papilloma virus (HPV) therein (Karina Araujo Aires et al., Appl. Environ. Microbiol. Vol. 72, pp 745-752, 2006), and the confirmation of the disease-treating effects of a lactic acid bacterial strain which secrets and expresses IL-2 (interleukin-2) (Lothar Steidler et al., Nat. Biotechnol. Vol. 21, pp 785-789, 2003).

As described above, the development of various applications of lactic acid bacteria expressing target proteins, and scientific studies on the lactic acid bacteria, have been actively conducted, there are still problems in that the expression levels of the target proteins are insufficient and in that, when a protein obtained using an inducible expression promoter is administered in vivo, sustained expression of the protein may not be possible.

In addition, cell surface display or cell surface expression refers to a technique by which a protein or a peptide is fused with an appropriate surface anchoring motif and expressed on the surface of Gram-negative or Gram-positive bacteria, fungus, yeast, or animal cells (Lee S. Y., et al., Trends Biotechnol., 21:4552, 2003). The first cell surface display technique was developed in 1980s using phage having a relatively simple surface, and is a technique in which a peptide or a small protein is fused with pIII of filamentous phage and expressed. Thus, the first cell surface display technique was named the surface-expression system. Cell surface display using phage has been used for screening of antibodies, epitopes, and high-affinity ligands, but has a limitation in that the size of protein that can be displayed on the phage surface is relatively limited. Thus, as an alternative thereto, cell surface expression using bacteria has been developed. This cell surface display is a technique in which a foreign protein is stably expressed on the microbial surface by using a surface protein of a microorganism such as bacteria or yeast as a surface anchoring motif.

In order to express a foreign protein on the cell surface using an outer membrane protein of a specific organism, a suitable surface protein and the foreign protein should be linked with each other at the gene level to form a fusion protein, and the fusion protein should stably pass through the cell inner membrane and should be attached to and maintained on the cell surface. To this end, a protein having the following properties is preferably used as the surface anchoring motif. Namely, (1) the protein has, at the N-terminus, a secretion signal capable of passing through the cell inner membrane; (2) the protein should have a targeting signal which can be stably attached onto the cell outer membrane; (3) the protein can be expressed on the cell surface in large amounts within the range that does not adversely affect the growth of cells, so that the protein can show high activity; and (4) the protein should be able to be stably expressed regardless of the size thereof such that it can be used in various reactions (Georgiou et al., TIBTECH, 11:6, 1993). In addition, this surface anchoring motif also needs to be genetically engineered such that it is inserted into the N-terminus, C-terminus or central portion of the outer membrane protein on the surface of a host cell (Lee et al., TIBTECH, 21:45-52, 2003).

In order for a protein to be expressed on the bacterial surface, the protein should have, in the primary sequence thereof, a secretion signal enabling the protein biosynthesized in the cell to pass through the cell membrane. In addition, in the case of Gram-negative bacteria, the protein should pass through the inner cell membrane and the cell membrane space, should be inserted into and attached to the outer cell membrane, and should be anchored onto the membrane so as to protrude outward from the membrane. In the case of bacteria, examples of these proteins that have a secretion signal and a targeting signal for protein anchoring to the cell surface include surface proteins, special enzymes, and toxin proteins. In fact, if the secretion signals and target signals of these proteins are used together with proper promoters, the proteins can be successfully expressed on the bacterial surface. Bacterial surface proteins used for surface expression of foreign proteins can be broadly divided into four types: outer membrane protein, lipoprotein, secretory protein, and cell surface organ protein. now, attempts have been made to express necessary foreign proteins on the bacterial surface using surface proteins present mainly in Gram-negative bacteria, for example, LamB, PhoE, and OmpA. However, when these proteins are used, a foreign protein is inserted into the protruding loop on the cell surface, and thus the protein size that can be structurally inserted is limited. Since the C- and N-termini of the foreign protein to be inserted should be located sterically close to each other, and thus when they are distant, a problem arise in that the two termini are brought close to each other by a linking peptide.

In fact, when LamB or PhoE was used, the insertion of a foreign polypeptide consisting of 50 to 60 or more amino acids resulted in structural limitations, so that a stable membrane protein was not formed [Charbit et al., J. Immunol., 139:1658-1664 (1987); Agterberg et al., Vaccine, 8:85-91 (1990)]. Although there is also a case in which OmpA was used to insert a foreign protein into the protruding loop, only some OmpA fragments containing a minimal targeting signal capable of being anchored to the outer membrane were used in order to overcome the structural limitations. There is a case in which beta-lactamase was linked to the C-terminus of the OmpA target signal by this method was expressed on the cell surface.

In addition, in recent years, attempts have been made for surface expression using ice-nucleation protein (INP) derived from *Pseudomonas* sp. as an outer membrane protein of Gram-positive bacteria [Jung et al., Nat, Biotechnol, 16:576-560 (1998), Jung et al., Enzyme Microb. Technol, 22 (5): 348-354 (1998), Lee et al., Nat. Biotechnol, 18:645-648 (2000)]. Jung et al. fused levansucrase to the C-terminus of an ice-nucleation protein consisting of an N-terminus, a central repeating region and the C-terminus, fused carboxymethylcellulase to the C-terminus of an ice-nucleation protein consisting of an N-terminus and the C-terminus without a central repeating region, induced surface expression of each of levansucrase and carboxymethylcellulase, and measured the activity of each of the enzymes. Lee et al. fused hepatitis B virus surface antigen and hepatitis C virus core antigen to each terminus of an ice-nucleation protein consisting of either an N-terminus or an N-terminus and a C-terminus, and expressed the antigens on the surface of an *E. coli* or *Salmonella typhi* Ty21a strain, and then confirmed that these antigens may be used as a complex live vaccine.

Lipoproteins are also used as surface proteins for surface expression. In particular, the lipoprotein of *E. coli* has a secretion signal at the N-terminus thereof, and can pass through the cell inner membrane, and L-cysteine at the terminus thereof is attached directly to the cell outer membrane lipid or inner membrane lipid through a covalent bond. The N-terminus of the main lipoprotein Lpp is bound to the outer cell membrane and the C-terminus thereof is bound to the cell wall (peptidoglycan, PG), and thus when the main lipoprotein Lpp is linked to a fragment of the outer membrane protein OmpA, it can stably secrete a foreign protein to the cell outer membrane and express the foreign protein on the cell surface [Francisco et al., Proc. Natl. Acad. Sci. USA, 489:2713-2717 (1992)]. TraT, another lipoprotein, was used to surface-express a peptide such as the C3 epitope of poliovirus using these properties of the lipoprotein [Felici et al., J. Mol. Biol., 222:301-310 (1991)]. In addition, cell wall-associated lipoprotein (PAL), whose exact function has not yet been identified, was also used for surface expression of a recombinant antibody [Fuchs et al., Bio/Technology, 9:1369-1372 (1991)]. In this case, the C-terminus of the PAL was linked to the cell wall, the N-terminus thereof was linked to a recombinant antibody, and the resulting fusion protein was expressed on the cell surface.

Secreted proteins that pass through the cell outer membrane may also be used as surface proteins. However, in the case of Gram-negative bacteria, secreted proteins are not developed, and only some secreted proteins have proteins that are involved in their specific secretion mechanisms and help to pass through the outer membrane. For example, pullulanase in the genus *Klebsiella* is a lipoprotein which is replaced with a lipid component at the N-terminus, is bound to the cell outer membrane and is then completely secreted into cell medium. Kornacker et al. expressed β-lactamase on the cell surface using the N-terminal fragment of pullulanase, but there was a disadvantage in that the expressed pullulanase-β-lactamase fusion protein was bound to the cell surface for a moment and was then released into the cell medium. Also, when alkaline phosphatase, a periplasmic space protein, was expressed using the N-terminal fragment of pullulanase, the alkaline phosphatase was not stably expressed on the cell surface because more than 14 proteins are involved in the secretion thereof [Kornacker, et al., Mol. Microl., 4:1101-1109 (1990)].

IgA protease, derived from the pathogenic microorganism *Neisseria* and having a unique secretion mechanism, has, in the C-terminal fragment thereof, a signal by which the N-terminal protease is anchored to the outer cell membrane. After the protease reaches the outer cell membrane and protrudes from the cell surface, the protease is secreted into cell medium by self hydrolysis. Using this IgA protease fragment, Klauser et al. stably expressed a 12-kDa cholera toxin B subunit on the cell surface [Klauser et al., EMBO J., 9:1991-1999 (1990)]. However, secretion of the fusion protein was inhibited due to protein folding that occurred in the periplasmic space during the secretion process.

In addition, in the case of Gram-negative bacteria, cell organelles, which are present on the surface structures and may be applied to surface expression, include flagella, pili and fimbriae. Cholera toxin B subunit and other peptides derived from hepatitis B virus were expressed stably using flagellin which is a constituent subunit of flagella, and these peptides strongly reacted with the respective antibodies [Newton et al., Science, 244:70-72 (1989)]. As a result of attempting to express foreign peptides on the cell surface using fimbrilin which is a constituent protein of fimbria that looks like a thread, only small peptides were successfully expressed [Hedegaard et al., Gene, 85:115-124 (1989)].

In addition to the above-described attempt to surface-express a foreign protein by a surface protein of Gram-negative bacteria, surface expression using a surface protein of Gram-positive bacteria was recently attempted [Samuelson et al., J. Bacteriol., 177:1470-1476 (1995)]. This attempt also requires a secretion signal capable of passing through the inner cell membrane and a surface anchoring motif which is attached to the cell membrane. In fact, there is a case in which a malaria blood stage antigen consisting of 80 amino acids and an albumin-associated protein derived from *Streptococcus* protein G were effectively expressed on the surface of Gram-positive bacteria using a *Staphylococcus hyicus*-derived lipase as a secretion signal and using *Staphylococcus aureus*-derived protein A as a membrane anchoring motif.

Through studies on the expression of proteins on the surfaces of Gram-negative and positive bacteria, many useful protein expression systems have been developed and have been applied for patent protection in the United States, Europe, and Japan. Among them, five cases (WO9504069, WO9324636, WO9310214, EP603672 and U.S. Pat. No. 5,356,797) related to the use of outer membrane proteins derived from Gram-negative bacteria were found, and one case (WO9410330) related to the use of the cell surface organelle pili was found, and one case related to the use of cell surface lipoprotein was also found.

In order to express a foreign protein on the cell surface using a bacterial outer membrane protein as described above, a suitable outer membrane protein and the foreign protein should be linked with each other at the gene level to form a fusion protein, and the fusion protein should stably pass through the inner cell membrane and should be attached to and maintained on the outer cell membrane. However, a surface anchoring motif that satisfies all of the above-described conditions has not been developed yet, and the state of the art to date remains at a level that overcome the disadvantages of the above-described cases.

Meanwhile, the present inventors previously developed a new vector which effectively expresses a foreign protein on the microbial surface using, as a new surface anchoring motif, a poly-gamma-glutamate synthetase complex gene (pgsBCA) derived from the *Bacillus subtilis* var. *Chungkookjang* strain, and a method of expressing a target protein on the surface of a microorganism transformed with the vector (Korean Patent No. 0469800).

Accordingly, the present inventors have believed that, if a vector capable of stably and highly expressing an antigen or an epitope on lactic acid bacteria using the surface anchoring motif disclosed in the above-described patent is developed, it is possible to produce a vaccine which is human-compatible and can effectively induce immune response, because the antigen is exposed to the surface of lactic acid bacteria. Based on this belief, the present inventors have performed a process of screening a promoter capable of highly expressing a target protein on lactic acid bacteria, and as a result, have found that, when a galactose mutarotase gene promoter is used, gene expression is improved compared to when a conventional promoter is used. Furthermore, the present inventors have conducted extensive studies on the use of a poly-gamma-glutamate synthetase gene (pgsA) derived from a *Bacillus* sp. strain as a new surface anchoring motif, and as a result, have developed a new vector which effectively expresses a foreign protein on the microbial surface using the pgsA gene, and a method of expressing a large amount of a foreign protein on the microbial surface using the pgsA gene, thereby completing the present invention.

DISCLOSURE

Technical Problem

A main object of the present invention is to provide a *Lactobacillus casei*-derived promoter that induces increased expression of a target gene.

Another object of the present invention is to provide an expression vector in which the promoter and a gene encoding the target protein are linked to each other.

Still another object of the present invention is to provide a microorganism transformed with the expression vector, and a method of producing a target protein using the transformed microorganism.

Yet another object of the present invention is to provide a method of producing a microbial vaccine using the transformed microorganism.

Still yet another object of the present invention is to provide a method including: an outer membrane protein, which is derived from a *Bacillus* sp. strain and involved in the synthesis of poly-gamma-glutamate, as a surface anchoring motif capable of expressing a large amount of a foreign promoter on the microbial surface; constructing a surface expression vector for expressing a target protein, which may express a foreign protein or peptide on the microbial surface using the selected outer membrane protein; and efficiently expressing a foreign protein on the surface of a transformant obtained by transformation with the surface expression vector.

Technical Solution

To achieve the above objects, the present invention provides a galactose mutarotase gene promoter derived from *Lactobacillus casei*.

In the present invention, the promoter may be represented by SEQ ID NO: 1.

The present invention also provides an expression vector in which a target gene is linked to an end of the promoter, and a microorganism transformed with the expression vector.

The present invention also a microbial surface expression vector in which the promoter, a poly-gamma-glutamate synthetase complex gene and a gene encoding a target protein are linked to one another, and a microorganism transformed with the expression vector.

In the present invention, the target protein may be an antigen. Specifically, the target protein may be any one selected from the group consisting of hormones, hormone analogs, enzymes, enzyme inhibitors, signaling proteins or fragments thereof, antibodies or fragments thereof, single chain antibodies, binding proteins, binding domains, peptides, antigens, adhesion proteins, structural proteins, regulatory proteins, toxin proteins, cytokines, transcription regulatory factors, coagulation factors, and plant biodefense-inducing proteins.

In the present invention, the poly-gamma-glutamate synthetase complex gene may be any one or more of pgsA, pgsB and pgsC.

The present invention also provides a method of expressing a target protein on the microbial surface by culturing the transformed microorganism.

The present invention also provides a method for producing a microbial vaccine, the method including steps of: (a) expressing an antigen on the microbial surface by culturing a microorganism transformed with the microbial surface expression vector; and (b) recovering the microorganism having the antigen expressed on the surface thereof.

To achieve the above objects, the present invention provides a surface expression vector for expressing a target protein, the surface expression vector including: a gene pgsA encoding a poly-gamma-glutamate synthetase complex; and a gene encoding the target protein.

In the present invention, the gene pgsA may be derived from a *Bacillus* sp. strain which produces poly-gamma-glutamate.

In the present invention, the gene pgsA encoding the poly-gamma-glutamate synthetase complex may have the nucleotide sequence of any one of SEQ ID NOs: 18 to 22 and 29 to 31. Preferably, the gene pgsA encoding the poly-gamma-glutamate synthetase complex may have the nucleotide sequence of any one of SEQ ID NOs: 18 to 21 and 29 to 31.

In the present invention, a linker may be inserted into the terminus of the gene pgsA encoding the poly-gamma-glutamate synthetase complex, and the gene encoding the target protein may be inserted into the inserted linker.

In the present invention, the target protein may be one in which a portion of the amino acid sequence of the target protein has been removed or mutated in a site-directed manner so as to favor surface expression.

The present invention also provides a microorganism transformed with the surface expression vector. In the present invention, a microorganism used for the transformation may be a microorganism modified so that it does not produce an intracellular or extracellular protease, which is involved in degradation of the expressed target protein, in order to favor cell surface expression of the target protein.

In the present invention, the microorganism may be lactic acid bacteria. In the present invention, examples of the lactic acid bacteria include *Lactobacillus* sp., *Streptococcus* sp., and *Bifidobacterium* sp. Typically, as the host, the *Lactobacillus* sp. may be selected from among *L. acidophilus, L. casei, L. plantarum, L. ferementum, L. delbrueckii, L. johnsonii* LJI, *L. reuteri*, and *L. bulgaricus*; the *Streptococcus* sp. may be *S. thermophilus*; and the *Bifidobacterium* sp. may be selected from among *B. infantis, B. bifidum, B. longum, B. psuedolongum, B. breve, B. lactis* Bb-12, and *B. adolescentis*. More preferably, the microorganism is *Lactobacillus* sp.

The present invention also provides a method for cell surface expression of a target protein, the method including steps of: expressing the target protein on the cell surface by culturing the transformed microorganism; and recovering cells having the target protein expressed on the surface thereof.

In the present invention, the target protein may be any one selected from the group consisting of hormones, hormone analogs, enzymes, enzyme inhibitors, signaling proteins or fragments thereof, antibodies or fragments thereof, single chain antibodies, binding proteins, binding domains, peptides, antigens, adhesion proteins, structural proteins, regulatory proteins, toxin proteins, cytokines, transcription regulatory factors, coagulation factors, and plant biodefense-inducing proteins.

The present invention also provides a method of inducing humoral immunity or cellular immunity by administering cells, produced by the above-described method and having an antigen expressed on the surface thereof, to vertebrates other than humans.

The present invention also provides a method of producing an antibody in vertebrates other than humans, the method including: inducing an immune response by administering cells, produced by the above-described method and having an antigen expressed on the surface thereof, to the vertebrates; and recovering an antibody produced by the immune response.

The present invention also provides a surface expression vector for expressing a target protein, wherein the vector is applied to Gram-negative or Gram-positive bacteria.

The present invention also provides a method of expressing a target protein on the surface of a Gram-negative or Gram-positive host cell, the method including steps of: (a) constructing a recombinant vector by inserting a gene encoding the target protein into a microbial surface expression vector; (b) transforming the Gram-negative or Gram-positive host cell with the recombinant vector; and (c) expressing the target protein on the surface of the transformed host cell by culturing the transformed host cell.

Advantageous Effects

The present invention provides a *Lactobacillus casei*-derived galactose mutarotase promoter capable of highly expressing a target protein on lactic acid bacteria, and an expression vector containing the promoter. Since the vector contains a gene which anchors the target protein to the microbial surface, the target protein may be effectively expressed on the cell surface in a transformant obtained using the vector, and thus lactic acid bacteria may be used as a vaccine vehicle.

In addition, the surface expression vector for expressing a target protein according to the present invention may stably express the target protein. The surface expression vector for expressing a target protein according to the present invention may express the target protein on the surface of a recombinant microorganism while constitutively expressing the target protein, and thus may be effectively used for the production of an antigen for producing a necessary vaccine.

BEST MODE

Example 2: Construction of Surface Expression Vector (pKV-Pgm-pgsA-EGFP) for EGFP Protein Expression Using Galactose Mutarotase Promoter In order to construct an expression vector for expression of an EGFP protein whose expression is induced by a galactose mutarotase promoter, a *Lactobacillus casei*-derived galactose mutarotase promoter was inserted into a vector having, as a replication origin, RepE which is replicable in *E. coli* and *Lactobacillus casei*, and then the surface anchoring motif pgsA derived from *Bacillus subtilis* var. *Chungkookjang* was introduced downstream of the promoter. Then, BamHI and XbaI restriction enzyme sites, which allow a target gene to be inserted into to the carboxyl terminus of the pgsA gene, were added thereto, thus constructing a pKV-Pgm-pgsA vector containing the galactose mutarotase promoter. As the pgsA gene, the pgsA gene disclosed in Korean Patent No. 0469800 was used.

EGFP gene was obtained by performing PCR using a synthesized EGFP gene fragment as a template and the primers of SEQ ID NOs: 4 and 5.

```
SEQ ID NO 4:
5'-TGGTGGATCCGTGAGCAAGGGCGAGGAGCTG-3'

SEQ ID NO 5:
5'-TGACTCTAGAACTAGTGTCGACGGTACCTTACTTGTA

CAGCTCGTCC-3'
```

Figure 2:
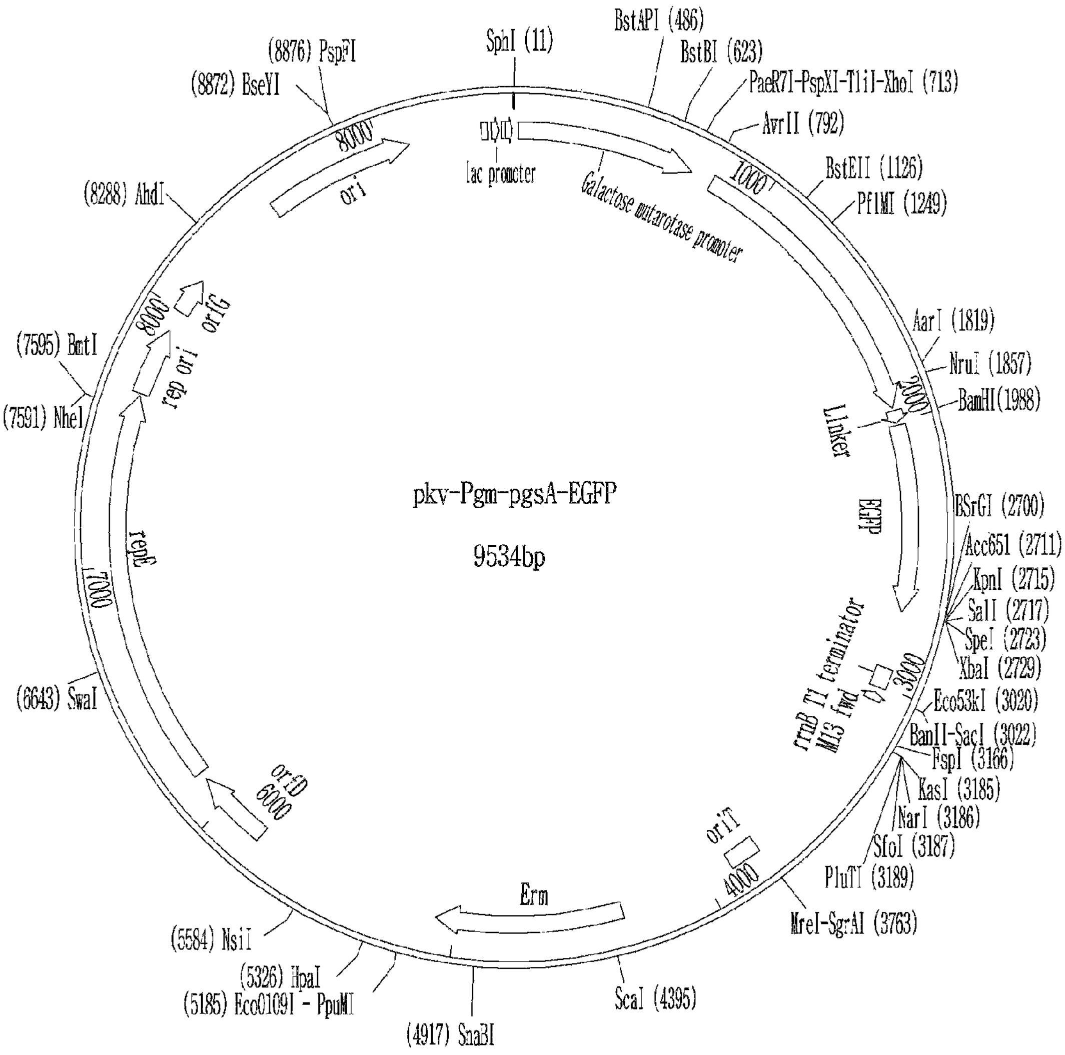
FIG. 2 shows a genetic map of a surface expression vector constructed using the galactose mutarotase promoter of the present invention.

As a result, a DNA fragment containing a BamHI restriction enzyme site at the 5' end thereof and an XbaI restriction enzyme site at the 3' end thereof was obtained. The obtained 755-bp DNA fragment containing the EGFP gene was cleaved with BamHI and XbaI and ligated to the C-terminus of the pgsA of the pKV-Pgm-pgsA vector, thus constructing the expression vector pKV-Pgm-pgsA-EGFP which can express the EGFP protein on the cell surface when being transformed into a lactic acid bacteria host (FIG. 2).

MODE FOR INVENTION

In one aspect, the present invention is directed to a galactose mutarotase gene promoter derived from *Lactobacillus casei.*

In the present invention, in order to obtain the galactose mutarotase gene promoter, the genome of *Lactobacillus casei* was amplified by a PCR method, and a 700-bp promoter (SEQ ID NO: 1) derived from *Lactobacillus casei* was isolated using a gene cloning technique. The galactose mutarotase promoter of the present invention is a promoter that induces expression of the galactose mutarotase gene present in *Lactobacillus casei*. Generally, a promoter contains a region to which RNA polymerase binds to induce the initiation of transcription, and the degree of RNA synthesis is determined depending on the nucleotide sequence of the promoter. For this reason, the expression level of a gene may vary depending on the kind of promoter.

In order to measure the expression induction ability of the promoter of the present invention, an EGFP gene was inserted into each of an expression vector containing said promoter and an expression vector containing a conventional aldolase promoter, and *Lactobacillus casei* was transformed with each of the constructed vectors. Then, the expression level of EGFP, the expression of which has been induced by each of the promoters, was measured through Western blotting. As a result, it was confirmed that the expression level of EGFP in the transformant obtained using the vector containing the galactose mutarotase effectively increased, and that the expression-inducing ability of the promoter of the present invention was also stronger than that of the conventional aldolase promoter.

In another aspect, the present invention is directed to an expression vector containing the galactose mutarotase promoter and a gene encoding a target protein, and a microorganism transformed with the expression vector.

In general, an expression vector minimally requires a promoter enabling transcription, a gene expressing a target protein downstream of the promoter, a gene which may be amplified by self-replication in a microorganism, and a selection marker gene for selecting a target vector, and said genes except for the target gene may vary depending on the backbone of the vector and a selected host cell. The genes minimally required in vector construction are widely known to those skilled in the art and may be easily selected depending on the expression conditions and intended use of a target gene. Generally, the backbone of the vector may have a replication origin of pWV01 or pAMβ1, but the scope of the present invention is not limited thereto.

Various methods and means may be used to introduce a vector or DNA sequence for expressing not only a target protein, but also a gene containing a regulatory region, into an appropriate host cell. For example, biochemical methods such as transformation, transfection, conjugation, protoplast fusion and calcium phosphate precipitation, or physical methods such as DEAE (diethylaminoethyl) dextran and electroporation, may be used.

After the expression vector is introduced into an appropriate host cell, only transformants may be screened using conventional techniques known in the art. In other words, transformants containing the vector capable of expressing a target gene may be screened using an antibiotic-containing selection medium suitable for the growth of host cells.

In still another aspect, the present invention is directed to a microbial surface expression vector in which the galactose mutarotase promoter, a poly-gamma-glutamate synthetase complex gene and a gene encoding a target protein are linked to one another, and a microorganism transformed with the surface expression vector.

A poly-gamma-glutamate synthetase complex gene, which is a surface anchoring motif, is contained downstream of the promoter, in which the surface anchoring motif is positioned between the promoter and the target protein in the DNA sequence of the vector. The gene of the surface anchoring motif plays a decisive role in the surface expression of the target gene, because it is linked to the initial portion of the target protein so as to induce the expressed protein to bind to lipid of the cell membrane, after it is encoded into the amino acid sequence. A method of linking the gene of the surface anchoring motif with the promoter and the target gene may be performed by conventional techniques which may be easily practiced by those skilled in the art, including PCR, restriction enzyme digestion and ligation.

In the present specification, the term "host" or "microorganism" refers to probiotic Gram-positive lactic acid bacteria. Common selection criteria for probiotic microorganisms include the following: (i) a microorganism derived from humans; (ii) stability against bile, acid, enzyme and oxygen; (iii) ability to adhere to intestinal mucosa; (iv) colonization potential in the human gastrointestinal tract; (v) production of antimicrobial substances; and (vi) demonstrable efficacy and safety. On the basis of such criteria, it is apparent that lactic acid bacteria are biocompatible and harmless to the human body. Thus, when transformants which use lactic acid bacteria as a host are applied to the human body in order to deliver a gene or protein for preventing or treating disease, a step of detoxifying bacterial strains is not required, unlike a conventional method of producing vaccines using bacterial strains.

In the present invention, examples of the microorganism include *Lactobacillus* sp., *Streptococcus* sp., and *Bifidobacterium* sp. Typically, as the host, the *Lactobacillus* sp. may be selected from among *L. acidophilus, L. casei, L. plantarum, L. ferementum, L. delbrueckii, L. johnsonii* LJI, *L. reuteri*, and *L. bulgaricus*; the *Streptococcus* sp. may be *S. thermophilus*; and the *Bifidobacterium* sp. may be selected from among *B. infantis, B. bifidum, B. longum, B. psuedolongum, B. breve, B. lactis* Bb-12, and *B. adolescentis*. More preferably, the microorganism is *Lactobacillus* sp.

In the present invention, an expression vector (pKV-Pgm-pgsA-EGFP) that expresses EGFP was constructed, which contains a nucleotide sequence including the promoter the promoter linked to the surface anchoring motif pgsA and may express the EGFP gene as a target gene, and a transformant that expresses EGFP was constructed by inserting the expression vector into *Lactobacillus casei*.

The target protein which is expressed by the promoter of the present invention, which has an improved gene expression ability, is expressed on the cell surface, and thus the transformed microorganism of the present invention may be used as a vaccine.

In yet another aspect, the present invention is directed to a method of producing a microbial vaccine using lactic acid bacteria transformed with the surface expression vector.

Vaccines are drugs that are used to stimulate the immune system using living organisms for the purpose of preventing diseases. Immune activation refers to a process of efficiently removing antigens by antibody production, stimulation of T-lymphocytes, or stimulation of other immune cells (e.g., macrophages) in organisms. A detailed overview of immunology relating to such details will be easily understood by those skilled in the art (Barrett, J. T., Textbook of Immunology, 1983).

A transformed microorganism vaccine expressing a target protein as an antigen may be administered to mammals, preferably human beings.

The preparation of the vaccine composition may be performed using standard techniques. A dose suitable for administration to a subject varies depending on the antigenicity of gene products and may be an amount in which the vaccine can sufficiently induce typical immune responses. The dose can be easily determined through usual experimental procedures. The typical initial dose of the vaccine is 0.001 to 1 mg antigen/kg of body weight. If necessary, the dose can be increased so as to offer a preferred level of protection, or the vaccine is used in a multiple dose. The dose can be determined by those skilled in the art and can also vary depending on various factors such as formulation method, administration mode, the subject's age, body weight and sex, pathological conditions, diet, administration duration, administration route, excretion rate, and response sensitivity.

In order for the vaccine to be effective in producing an antibody, an antigenic substance should be released in vivo so that the antibody-producing mechanism in the vaccinated subject can be realized. Thus, a microbial carrier for a gene product must be preferentially introduced in vivo for immune responses. In order to stimulate a preferred response by an antigen which is presented by the transformant of the present invention, the vaccine is preferably administered orally, by gastrointestinal intubation, or directly to the intestines or lungs in the form of aerosol, even though administration methods such as intravenous injection, intramuscular injection, or subcutaneous injection are also possible.

For oral administration of the vaccine composition to a subject, the vaccine composition is preferably provided in a lyophilic form, for example, a capsule form. The capsule is provided as an enteric coating containing Eudragate S, Eudragate L, cellulose acetate, cellulose phthalate or hydroxyprolylmethyl cellulose. The capsule may be used as it is or may be administered after it has been reconstituted into a lyophilic material such as a suspension. The reconstitution is preferably performed in a buffer having a pH value suitable for the survival of the transformed microorganism. In order to protect the transformed microorganism and the vaccine from gastric acid, it is preferable to administer a sodium bicarbonate formulation every time before administering the vaccine. The vaccine can be selectively prepared for parenteral administration, intranasal administration or intramammary administration.

The transformed lactic acid bacteria containing the promoters of the present invention and containing the gene encoding the target protein capable of acting as an antigen may exhibit the desired efficacy while forming colonies in the mucous membrane of the digestive tract, so that the desired efficacy can be obtained. Also, the above-described lactic acid bacteria may co-administer the selected antibiotics in the vector for smooth colony formation while maintaining the desired transformation properties, and may control the development of undesired lactic acid bacteria having no vector, which can be developed during cell division in the transformant.

The process for selection of the antibiotics can be easily performed using any conventional technique known in the art, and the selected antibiotics, which may be used in the above process, may vary depending on the antibiotic gene contained in the expression vector.

In addition, in the present invention, improvement of the surface expression vector (pKV-Pald-PgsA-EGFP) constructed in Example 4 below was performed using PgsA gene fragments so that it could more stably exhibit a high gene expression level in the lactic acid bacteria host.

First, among PgsA fragments, PgsA fragments containing 1-60 a.a, 1-70 a.a, 1-80 a.a, 1-100 a.a and 1-188 a.a, respectively, were obtained by performing PCR using the surface expression vector (pKV-Pald-PgsA-EGFP) as a template and the primers of SEQ ID NOs: 8 to 17.

As a result, DNA fragments, containing an aldolase promoter and the respective PgsA motif fragments, were obtained. Each of the DNA fragments contained an SphI restriction enzyme site at the 5' end thereof and a BamHI restriction enzyme site ta the 3" end thereof. Each of the obtained DNA fragments was treated with SphI and BamHI to obtain fragments. In addition, it was confirmed that the PgsA1 to A5 motif fragments had the nucleotide sequences of SEQ ID NOs: 18 to 22, respectively.

Meanwhile, among PgsA fragments, PgsA fragments containing 25-60 a.a, 25-70 a.a and 25-100 a.a, respectively, were obtained by performing PCR using the surface expression vector (pKV-Pald-PgsA-EGFP) as a template and the primers of SEQ ID NOs: 23 to 28.

As a result, DNA fragments containing the respective PgsA motif fragments were obtained. Each of the fragments contained an EcoRV restriction enzyme site at the 5' end thereof and a BamHI restriction enzyme site at the 3' end thereof. The obtained DNA fragments were treated with EcoRV and BamHI to obtain fragments. In addition, it was confirmed that the PgsA motif fragments had the nucleotide sequences of SEQ ID NOs: 29 to 31, respectively.

An object of the present invention is to provide a method including: selecting an outer membrane protein, which is derived from a *Bacillus* sp. strain and involved in the synthesis of poly-gamma-glutamate, as a new surface anchoring motif capable of expressing a large amount of a foreign protein on the microbial surface; constructing a surface expression vector capable of expressing a foreign protein or peptide on the microbial surface using the selected cell outer membrane protein; and efficiently expressing a foreign protein on the surface of a transformant obtained using the surface expression vector.

To achieve the above object, the present invention provides a microbial surface expression vector containing the gene pgsA encoding a poly-gamma-glutamate synthetase complex, and a strain transformed with the vector.

To achieve the above object, the present invention also provides a method of expressing a foreign protein on the surface of the transformed strain using the microbial surface expression vector.

The protein encoded by the gene pgsA is an outer membrane protein present in *Bacillus* sp., and is a protein which is involved in the synthesis of poly-gamma-glutamate which is an edible, water-soluble, anionic and biodegradable polymer produced from *Bacillus subtilis* IF03336 (Natto; Biochem. Biophy. Research Comm., 263, 6-12, 1999), *Bacillus licheniformis* ATCC9945 (Biotech. Bioeng. 57 (4), 430-437, 1998), *Bacillus anthracis* (J. Bacteriology, 171, 722-730, 1989), etc.

The outer membrane proteins isolated from *Bacillus subtilis* IF03336 consist of a total of 922 amino acids and are composed of pgsB, pgsC and pgsA. pgsB consists of 393 amino acids, pgsC consists of 149 amino acids, and pgsA consists of 380 amino acids. Ashiuchi et al. cloned the poly-gamma-glutamate synthetase gene derived from *Bacillus subtilis*, transformed the gene into *E. coli*, and observed the synthesis of the gene in the *E. coli* [Ashiuchi et al., Biochem. Biophy. Res. Communications, 263:6-12 (1999)].

However, the detailed role and function of the pgsA protein of the poly-gamma-glutamate synthetase complex have not yet been found. However, among the proteins of the complex, pgsB is an amide ligase system, and the specific amino acids at the N-terminus of pgsB interact with the cell membrane or cell wall, and pgsA has hydrophilic specific amino acid sequences at the N-terminus and C-terminus thereof. Thus, it is presumed that these amino acids have secretion signals, which can pass through the inner cell membrane with the help of pgsB, and targeting and adhesion signals.

The study conducted by the present inventors revealed that the outer membrane proteins which are involved in the synthesis of poly-gamma-glutamate has many advantages as a surface anchoring motif which expresses a foreign protein on the cell surface due to the primary amino acid sequence structures and characteristics thereof. The advantages are as follows. First, the outer membrane proteins which are involved in the synthesis of poly-gamma-glutamate may be expressed in large amounts on the cell surface for the synthesis and extracellular secretion of poly-gamma-glutamate. Second, the expressed outer membrane proteins which are involved in the synthesis of poly-gamma-glutamate are stably maintained even in the resting phase of the cell cycle. Third, structurally, pgsA protrudes from the cell surface. Fourth, the outer membrane proteins which are involved in the synthesis of poly-gamma-glutamate originate from the surfaces of Gram-positive bacteria and may be stably expressed on the surfaces of not only various Gram-positive bacteria but also Gram-negative bacteria.

An object of the present invention is to provide a useful vector capable of expressing a foreign protein on the bacterial surface using the characteristics of an outer membrane protein which is involved in the synthesis of poly-gamma-glutamate. In particular, the surface expression vector for expressing a target protein according to the present invention includes a secretion signal and a targeting signal, which are contained in the primary sequence of the outer membrane protein which is involved in the synthesis of poly-gamma-glutamate.

Another object of the present invention is to provide a method of expressing a foreign protein on the microbial surface using a surface expression vector which uses the characteristics of an outer membrane protein which is involved in the synthesis of poly-gamma-glutamate. In particular, the present invention provides a method for producing a foreign protein, which enables the foreign protein to be efficiently used without a cell disruption or protein isolation/purification process by expressing the foreign protein on the microbial surface using an outer membrane protein which is involved in the synthesis of poly-gamma-glutamate.

In the present invention, the term "target protein" or "foreign protein" refers to a protein that cannot normally exist in a transformed host cell expressing the protein. For example, when a virus-derived or tumor-derived protein is manipulated to be artificially expressed in lactic acid bacteria, the protein will be referred to as "foreign protein" or "target protein".

Preferably, examples of the target protein include, but are not limited to, infectious microorganisms, immune disease-derived antigens or tumor-derived antigens, for example, fungal pathogens, bacteria, parasites, helminths, viruses or allergy-causing substances. More preferably, examples of the antigen include tetanus toxoid, influenza virus hemagglutinin or nuclear protein, diphtheria toxoid, HIV gp120 or fragments thereof, HIV gag protein, IgA protease, insulin peptide B, *Spongospora subterranea* antigen, *Vibriose* antigen, *Salmonella* antigen, *Pneumococcus* antigen, RSV (respiratory syncytial virus) antigen, *Hemophilus influenza* outer membrane protein, *Streptococcus pneumoniae* antigen, *Helicobacter pylori* urease, *Neisseria meningitidis* pilin, *N. gonorrhoeae* pilin, melanoma associated antigens (TRP2, MAGE-1, MAGE-3, gp100, tyrosinase, MART-1, HSP-70, beta-HCG), human papilloma virus antigens including E1, E2, E6 and E7 derived from HPV-16, -18, -31, -35 or -45, CEA tumor antigen, normal or mutated ras protein, normal or mutated p53, Mucl, and pSA, as well as antigens well known in the art, which are derived from the followings: cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, Addison's disease, immunogens, allergen, cancers including solid and blood borne tumors, acquired immune deficiency syndrome, and factors involved in transplant rejection, such as kidney, heart, pancreas, lung, bone, and liver transplant rejections; and antigens inducing autoimmunity.

Therefore, the target protein produced by the surface expression method of the present invention may be used in various applications. These applications include effective production of antibodies and enzymes, as well as production of peptide libraries for screening antigens, adhesion or adsorption proteins and new physiologically active substances.

The scope of the present invention includes all surface expression vectors containing all kinds of genes which are involved in the synthesis of poly-gamma-glutamate, including genes encoding outer membrane proteins which are derived from a *Bacillus* sp. strain and involved in the synthesis of poly-gamma-glutamate.

In addition, the surface expression vector containing a poly-gamma-glutamate synthetase gene according to the present invention may be applied to all types of strains to express a foreign protein on the microbial surface. Preferably, the surface expression vector may be applied to Gram-negative bacteria, more preferably *E. coli, Salmonella typhi, Salmonella typhimurium, Vibrio cholera, Mycobacterium bovis*, and *Shigella*, and to Gram-positive bacteria, preferably *Bacillus, Lactobacillus, Lactococcus, Staphylococcus, Lysteria monocytogenes*, and *Streptococcus*. Methods of producing all types of foreign proteins using the above strains are included within the scope of the present invention.

If necessary, restriction enzyme recognition sites may be inserted into the N-terminus or C-terminus of the poly-gamma-glutamate synthetase gene, and surface expression vectors having these restriction enzyme sites inserted therein are all included within the scope of the present invention.

Specifically, the present invention provides the surface expression vectors pKV-Pald-pgsA1 to pKV-Pald-pgsA8 which contain the poly-gamma-glutamate synthetase gene pgsA derived from a *Bacillus* sp. strain and into which various foreign genes may be easily cloned using restriction enzyme recognition sites inserted into the C-terminus of pgsA.

The present invention provides the surface expression vectors pKV-Pald-pgsA1 to pKV-Pald-pgsA8 which contain the outer membrane complex pgsA among outer membrane protein complexes involved in the synthesis of poly-gamma-glutamate, and may express, on the surface of Gram-positive bacteria, an EGFP protein in the form of a fusion protein obtained by linking the N-terminus of the EGFP protein to the C-terminus of pgsA.

In particular, in one example of the present invention, the outer-membrane protein gene pgsA which is involved in the synthesis of poly-gamma-glutamate was obtained from *Bacillus subtilis* var. *Chungkookjang* (KCTC 0697BP), but constructing a vector using pgsA obtained from any *Bacillus* sp. strain, which produces poly-gamma-glutamate, or expressing a foreign protein on the microbial surface using the vector, is also included within the scope of the present invention. For example, constructing a vector using a pgsA gene derived from any strain, which has a sequence homology of at least 80% to the nucleotide sequence of the pgsA gene present in *Bacillus subtilis* var. *Chungkookjang*, or expressing a foreign protein on the microbial surface using the vector, is also included within the scope of the present invention.

In another example of the present invention, whether a protein is efficiently expressed on the *E. coli* cell surface was examined using enhanced Green fluorescent protein (EGFP) selected as a model protein. The "enhanced green fluorescent protein (EGFP)" is a gene that emits green light in vivo to enable easy observation of cells expressing the corresponding protein, and has the advantage of being capable of being observed under a fluorescence microscope. GFP is a green fluorescent protein originating from jellyfish (*Aequorea victoria*) and has been used as an important marker for gene expression in various research fields. EGFP is a mutant of GFP, results from substitution of leucine for phenylalanine at position 64 in the amino acid sequence of GFP and substitution of threonine for serine at position 65, and has the advantage of showing a stronger fluorescent signal than the original GFP The present inventors constructed surface expression vectors by inserting the EGFP gene into the above-described constructed recombinant vectors pKV-Pald-pgsA1 to pKV-Pald-pgsA8, transformed *Lactobacillus casei* with each of the surface expression vectors, and then cultured the transformed *Lactobacillus casei* to induce protein expression, and obtained a protein by collecting a certain amount of the culture. The obtained protein was analyzed by SDS-PAGE and subjected to Western blotting using anti-EGFP antibody, and as a result, it was confirmed that the EGFP protein was inserted successfully into the constructed recombinant vectors pKV-Pald-pgsA1 to pKV-Pald-pgsA8 and expressed on the cell surface.

In addition, in the above-mentioned examples, EGFP protein was used as a foreign protein, but any other proteins such as enzymes, antigens, antibodies, adhesion proteins or adsorption proteins may also be used as foreign proteins.

Hereinafter, the present invention will be described in more detail with reference to examples. It will be obvious to those skilled in the art that these examples serve merely to illustrate the present invention, and the scope of the present invention is not limited by these examples.

In particular, in the following examples, the pgsA gene was used as a motif for constructing a surface expression vector, but it will be obvious to those skilled in the art that the use of pgsB, pgsC or a combination thereof may also show results similar to those obtained in the use of pgsA, as disclosed in the previous patent application (WO2003/014360) filed in the name of the applicant.

In addition, in the following examples, surface expression vectors for application to Gram-positive bacteria were constructed and *Lactobacillus casei* was used as host cells, but it will be obvious to those skilled in the art that any Gram-positive bacteria other than *Lactobacillus casei* may be used as host cells, and Gram-negative bacteria and other bacteria other than Gram-positive bacteria may be transformed with the surface expression vectors.

Example 1: Construction of *Lactobacillus casei*-Derived Galactose Mutarotase Promoter A 700-bp DNA fragment corresponding to the promoter region of the galactose mutarotase gene was obtained by PCR from *Lactobacillus casei.*

To this end, *Lactobacillus casei* was cultured in basal MRS medium (containing 1% casein hydrolysate, 1.5% yeast extract, 2% dextrose, 0.2% ammonium citrate, 0.5% sodium acetate, 0.01% magnesium sulfate, 0.05% manganese sulfate and 0.2% dipotassium phosphate; Acumedia Manufacturers, Inc.), and $1\times10^9$ cultured *Lactobacillus casei* cells were disrupted to obtain a solution. The solution was used as a template for PCR.

Figure 1:
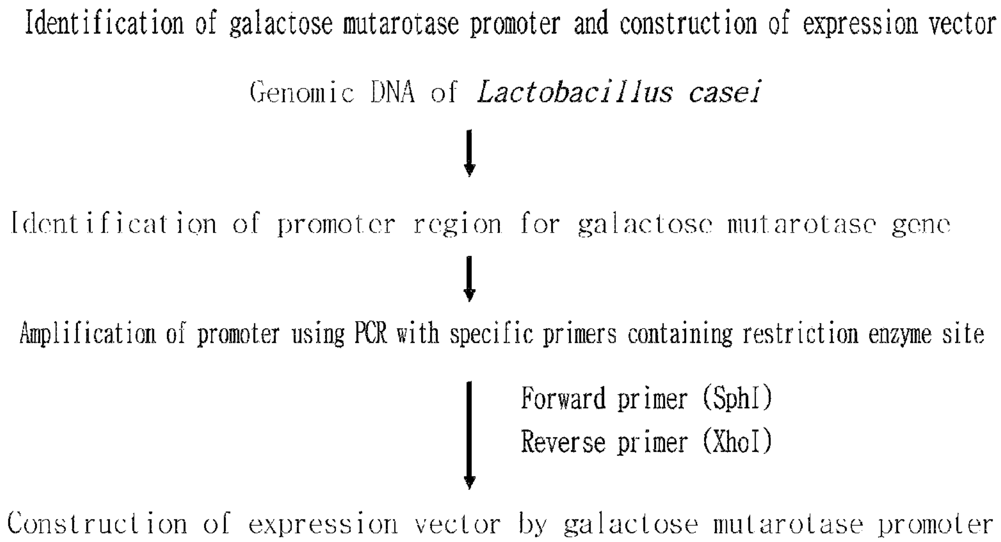
FIG. 1 shows a method of obtaining a galactose mutarotase promoter of the present invention.

In order to facilitate insertion into a vector in gene cloning, SphI and XhoI restriction enzyme sites were located at the ends of each of primers (SEQ ID NO: 2 and SEQ ID NO: 3). As a result of performing PCR using the primers, an amplification product (SEQ ID NO: 1) having a total length of 700 bp was obtained. The PCR amplification product was cloned into a pGEM-Teasy vector (Promega Co., USA), and the nucleotide sequence thereof was analyzed (FIG. 1).

```
SEQ ID NO 2:
5'-TACGGCATGCTTGAATTGGTTTCTTACGAT-3'

SEQ ID NO 3:
5'-TACGCTCGAGGTTGAATTACCTCCTAATAG-3'
```

Example 2: Construction of Surface Expression Vector (pKV-Pgm-pgsA-EGFP) for EGFP Protein Expression Using Galactose Mutarotase Promoter In order to construct an expression vector for expression of an EGFP protein whose expression is induced by the galactose mutarotase promoter, the *Lactobacillus casei*-derived galactose mutarotase promoter was inserted into a vector having, as a replication RepE which origin, is replicable in *E. coli* and *Lactobacillus casei*, and then the surface anchoring motif pgsA derived from *Bacillus subtilis* var. *Chungkookjang* was introduced downstream of the promoter. Then, BamHI and XbaI restriction enzyme sites, which allow a target gene to be inserted into to the carboxyl terminus of the pgsA gene, were added thereto, thus constructing a pKV-Pgm-pgsA vector containing the galactose mutarotase promoter. As the pgsA gene, the pgsA gene disclosed in Korean Patent No. 0469800 was used.

EGFP gene was obtained by performing PCR using a synthesized EGFP gene fragment as a template and the primers of SEQ ID NOs: 4 and 5.

```
SEQ ID NO 4:
5'-TGGTGGATCCGTGAGCAAGGGCGAGGAGCTG-3'

SEQ ID NO 5:
5'-TGACTCTAGAACTAGTGTCGACGGTACCTTACTTGTA

CAGCTCGTCC-3'
```

As a result, a DNA fragment containing a BamHI restriction enzyme site at the 5' end thereof and an XbaI restriction enzyme site at the 3' end thereof was obtained. The obtained 755-bp DNA fragment containing the EGFP gene was cleaved with BamHI and XbaI and ligated to the C-terminus of the pgsA of the pKV-Pgm-pgsA vector, thus constructing the expression vector pKV-Pgm-pgsA-EGFP which can express the EGFP protein on the cell surface when being transformed into a lactic acid bacteria host (FIG. 2).

Example 3: Analysis of Target Protein Expression and Intensity of Expression Induction Through Western Blotting In this Example, *Lactobacillus casei* was transformed with the expression vector pKV-Pgm-pgsA-EGFP constructed in Example 2. The transformed *Lactobacillus casei* was cultured, and expression of EGFP protein on the surface thereof was analyzed.

In order to examine the expression induction ability of the new galactose mutarotase promoter in comparison with a conventional aldolase promoter, expression vectors were constructed by linking an EGFP gene as a reporter gene to each of the promoters, and *Lactobacillus casei* was transformed with each of the expression vectors. In addition, the expression level of EGFP was measured through Western blotting.

First, the recombinant *Lactobacillus casei* transformed with the surface expression vector of the present invention was stationary-cultured in MRS medium (*Lactobacillus* MRS, Becton Dickinson and Company Sparks, USA) at 30° C. to induce surface expression of the EGFP protein.

Expression of the fusion protein was analyzed by subjecting the cultured *Lactobacillus casei* whole cells to SDS-polyacrylamide gel electrophoresis and to Western blotting using a specific antibody against EGFP.

Specifically, the recombinant *Lactobacillus casei* whole cells on which protein expression was induced were denatured with proteins obtained at the same cell concentration to prepare a sample. The sample was analyzed by SDS-polyacrylamide gel electrophoresis, and then the fractionated proteins were transferred to a PVDF (polyvinylidene-difluoride) membrane (Bio-Rad). The PVDF membrane having the proteins transferred thereto was blocked in blocking buffer (50 mM Tris-HCl, 5% skim milk, pH 8.0) for 1 hour, and then incubated for 1 hour with a 1:1,000 dilution of an anti-rabbit polyclonal primary antibody against EG0FP in blocking buffer. After completion of the incubation, the membrane was washed with buffer and incubated for 1 hour with a 1:10,000 dilution of HRP (horseradish peroxidase)-conjugated anti-rabbit secondary antibody in blocking solution. After completion of the incubation, the membrane was washed with buffer, and the washed membrane was color-developed with a substrate (Lumigen PS-3 acridan, $H_2O_2$) for about 2 minutes. Then, specific binding between the specific antibody against EGFP and the fusion protein was visualized by a CCD camera.

Figure 3:
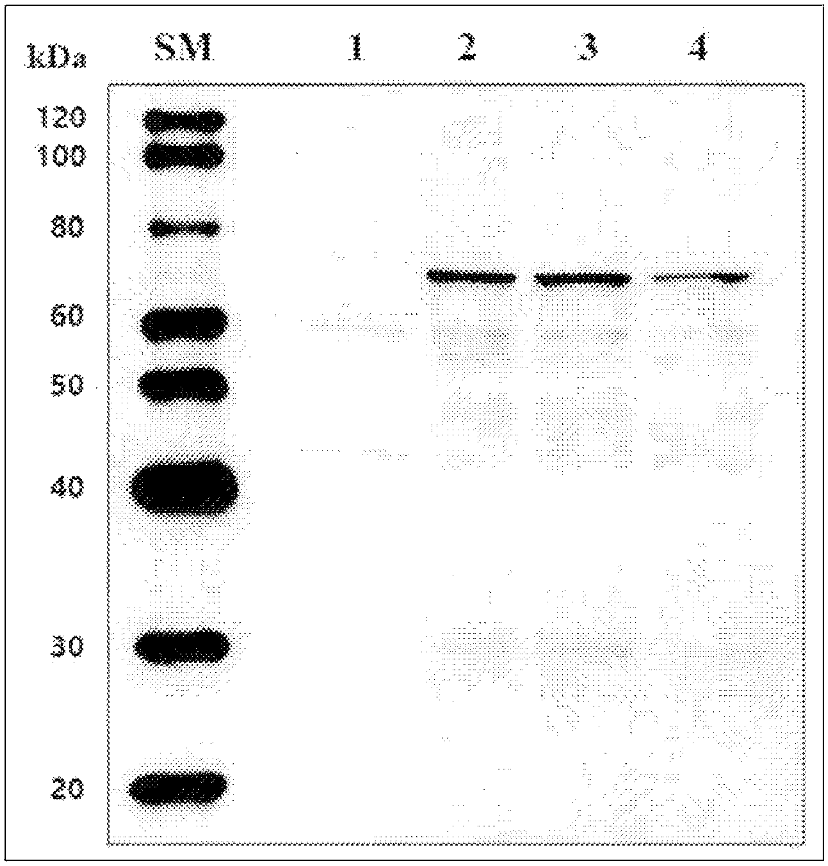
FIG. 3 shows the results of performing Western blotting to measure the expression level of a target protein by each promoter on lactic acid bacteria transformed with the expression vector of the present invention.

FIG. 3 shows the results of performing Western blotting to measure the expression level of the EGFP protein on the recombinant *Lactobacillus casei* whole cells transformed with the cell surface expression vector of the present invention. In FIG. 3, lane SM represents a protein size marker; lane 1 represents expression on *Lactobacillus casei* (empty vector); lanes 2 and 3 represent expression on *Lactobacillus casei* (pKV-Pgm-pgsA-EGFP); and lane 4 represents expression on *Lactobacillus casei* (pKV-Pald-pgsA-EGFP).

It was confirmed that the expression vector pKV-Pgm-pgsA-EGFP (lanes 2 and 3) of the present invention expressed the target protein and also showed a higher expression level of the target protein than the expression vector pKV-Pald-pgsA-EGFP (lane 4). This indicates that the galactose mutarotase promoter of the present invention can stably express the target protein present in the expression vector and can more strongly express the target protein than the aldolase promoter (FIG. 3).

Example 4: Observation of Expression of Two Target Proteins on Microbial Surface by Confocal Fluorescence Microscopy In order to examine the expression level of the surface expression vector of the present invention, fluorescence images were observed by confocal microscopy (Carl Zeiss LSM800).

The recombinant *Lactobacillus casei* transformed with the surface expression vector (pKV-Pgm-pgsA-EGFP) of the present invention was stationary-cultured in MRS medium (*Lactobacillus* MRS, Becton Dickinson and Company Sparks, USA) at 30° C. to induce surface expression of the EGFP protein. Next, the protein was allowed to bind to a specific antibody against EGFP, and then immunostained with Alexa488 (green). Then, expression of EGFP on the cell surface was observed by confocal microscopy.

Figure 4:
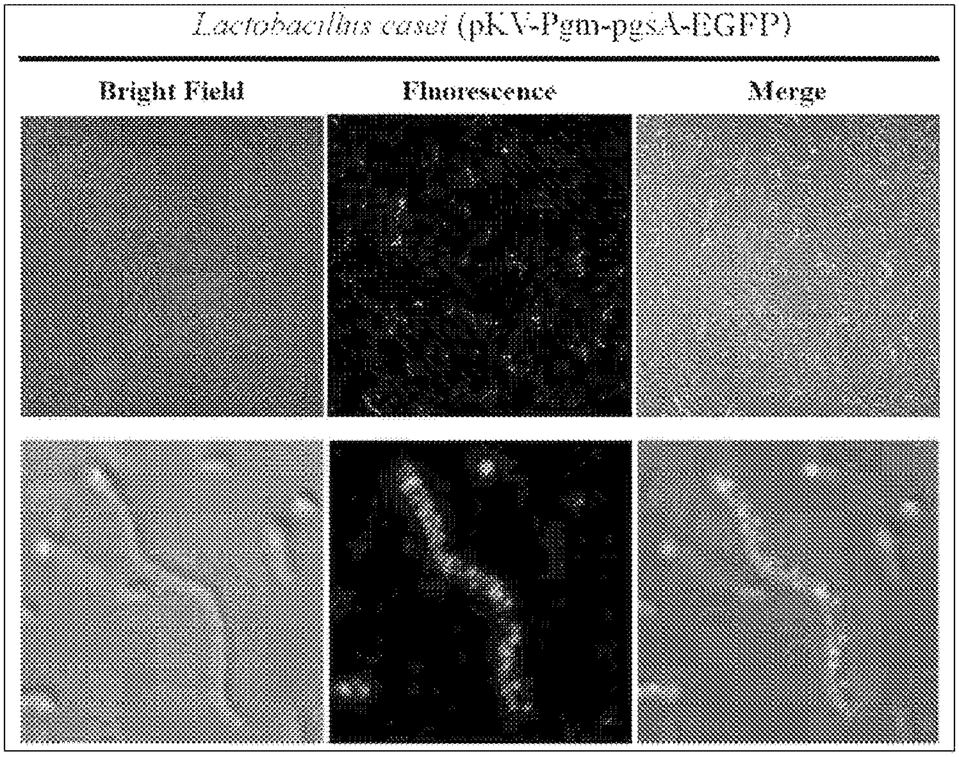
FIG. 4 shows the results of confocal fluorescence microscopic observation that indicate that a target protein is expressed on the microbial surface by the expression vector of the present invention.

As a result, as shown in FIG. 4, it could be confirmed that fluorescence was stably expressed in the recombinant *Lactobacillus casei* transformed with the surface expression vector of the present invention.

Thus, it is expected that the surface expression vector of the present invention may be transformed into lactic acid bacteria, does not require a strain-detoxifying step, unlike a conventional vaccine production method, and may more strongly express a target protein, indicating that it may be used for the production of a microbial vaccine.

Example 5: Construction of Surface Expression Vector pKV-Pald-pgsA-EGFP

To construct a vector for EGFP expression, using the surface expression vector pKV-Pald-PgsA-E7 (see Korean Patent No. 10-1471043), a gene encoding the EGFP protein was inserted into the C-terminus of PgsA of the surface expression vector to obtain the vector pKV-Pald-PgsA-EGFP capable of expressing the EGFP protein on the surface of lactic acid bacteria.

First, the HPV16 E7 gene fused with pgsA in the pKV-Pald-PgsA-E7 vector was removed, and a gene encoding EGFP was inserted into the vector. Using the synthesized EGFP gene fragment as a template, PCR was performed using the primers of SEQ ID NOs: 6 and 7.

```
SEQ ID NO 6:
5' TGGTGGATCCGTGAGCAAGGGCGAGGAGCTG 3'

SEQ ID NO 7:
5' TGACTCTAGAACTAGTGTCGACGGTACCTTACTTGTA

CAGCTCGTCC 3'
```

As a result, a 755-bp fragment containing the EGFP gene was obtained, which contains a BamHI restriction enzyme site at the 5' end thereof and an XbaI restriction enzyme site at the 3' end thereof. The obtained DNA fragment was cleaved by treatment with BamHI and XbaI restriction enzymes to obtain a 741-bp fragment.

pKV-Pald-PgsA-E7 was cleaved with BamHI and XbaI to remove the HPV16 E7 gene region and to obtain the vector region.

Figure 5:
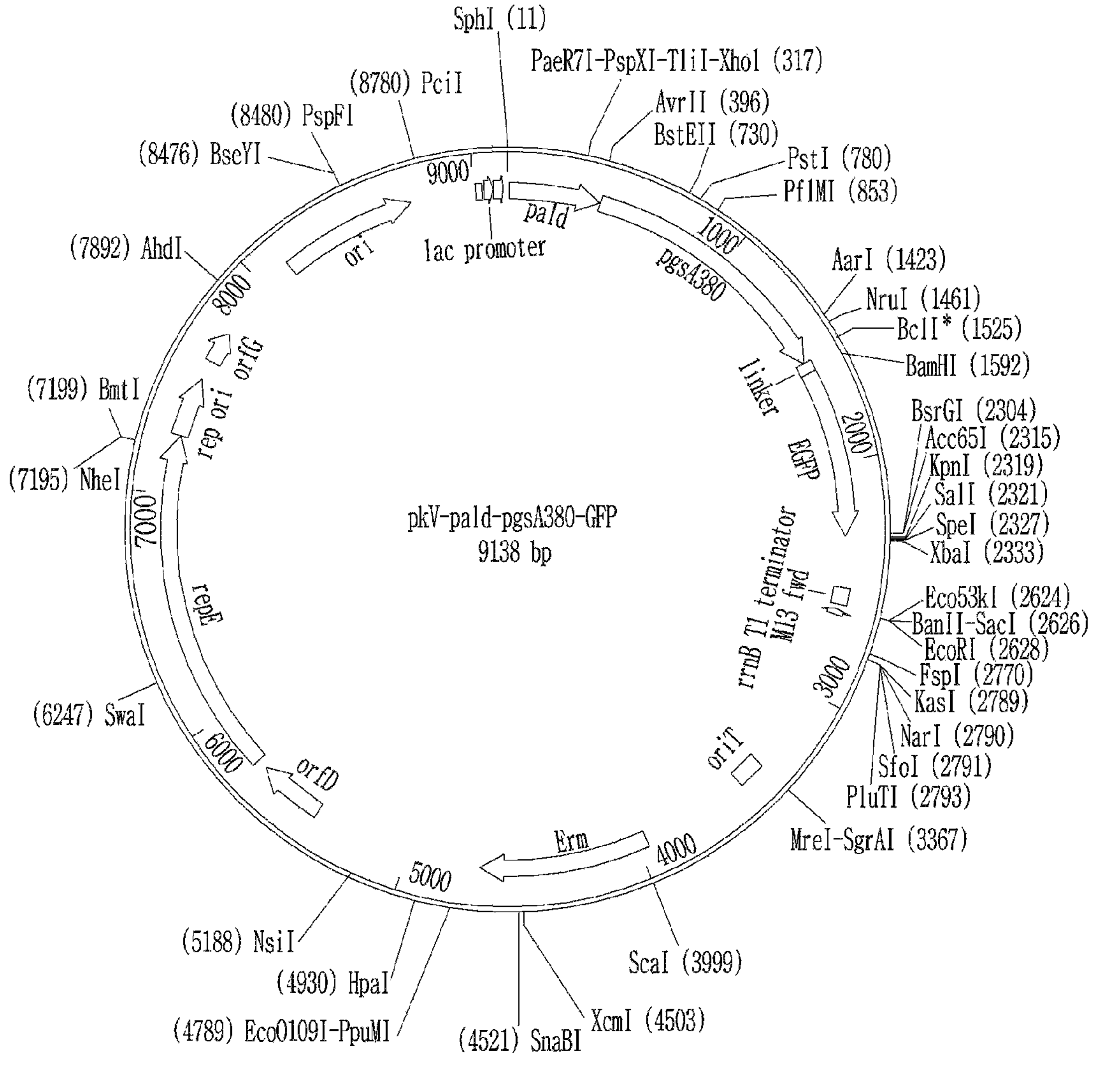
FIG. 5 shows a genetic map of the surface expression vector pKV-Pald-PgsA-EGFP according to the present invention, which uses *Lactobacillus casei* as a host.
Figure 6:
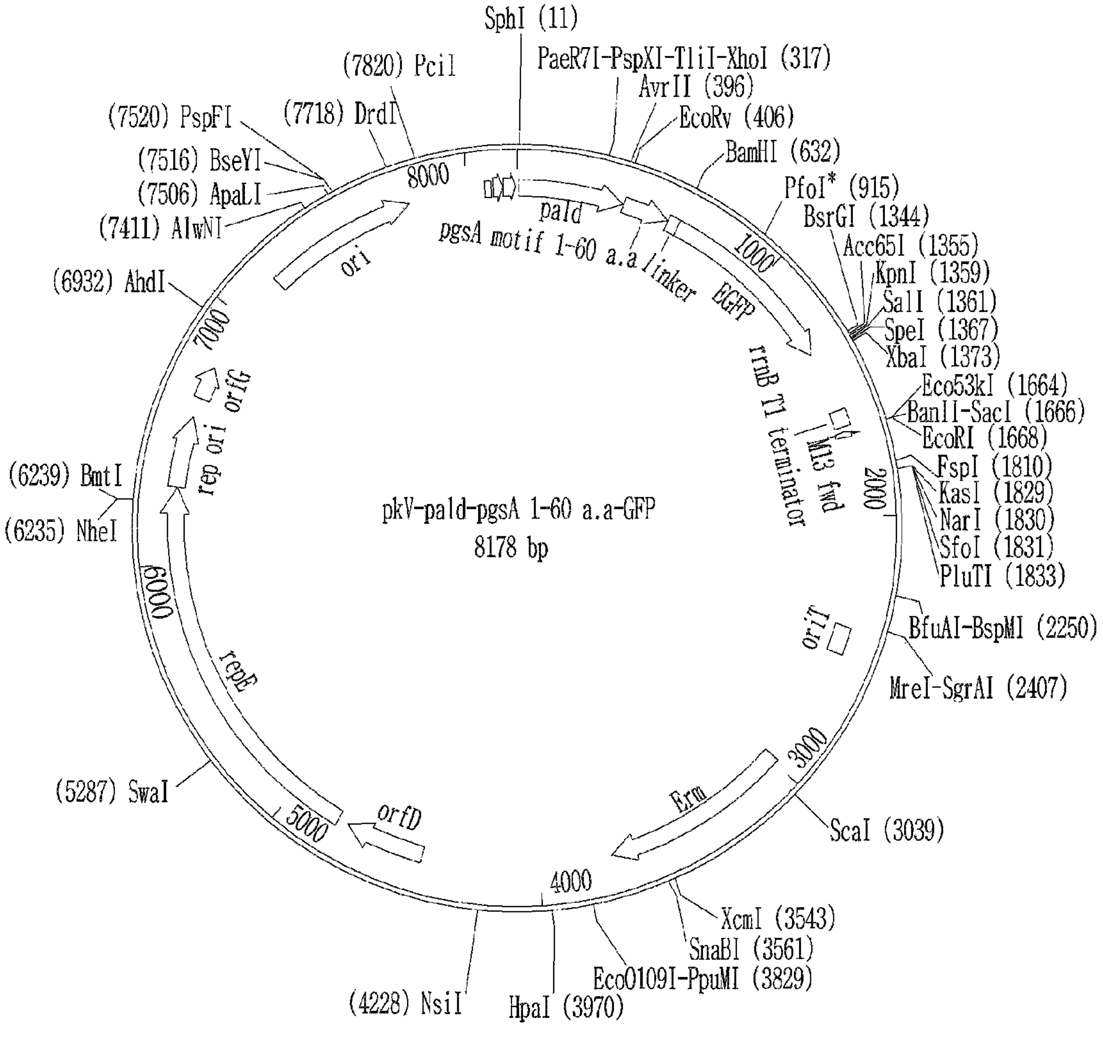
FIG. 6 shows a genetic map of the surface expression vector pKV-Pald-pgsA1 (pgsA motif 1-60 a.a)-EGFP according to the present invention, which uses *Lactobacillus casei* as a host.
Figure 7:
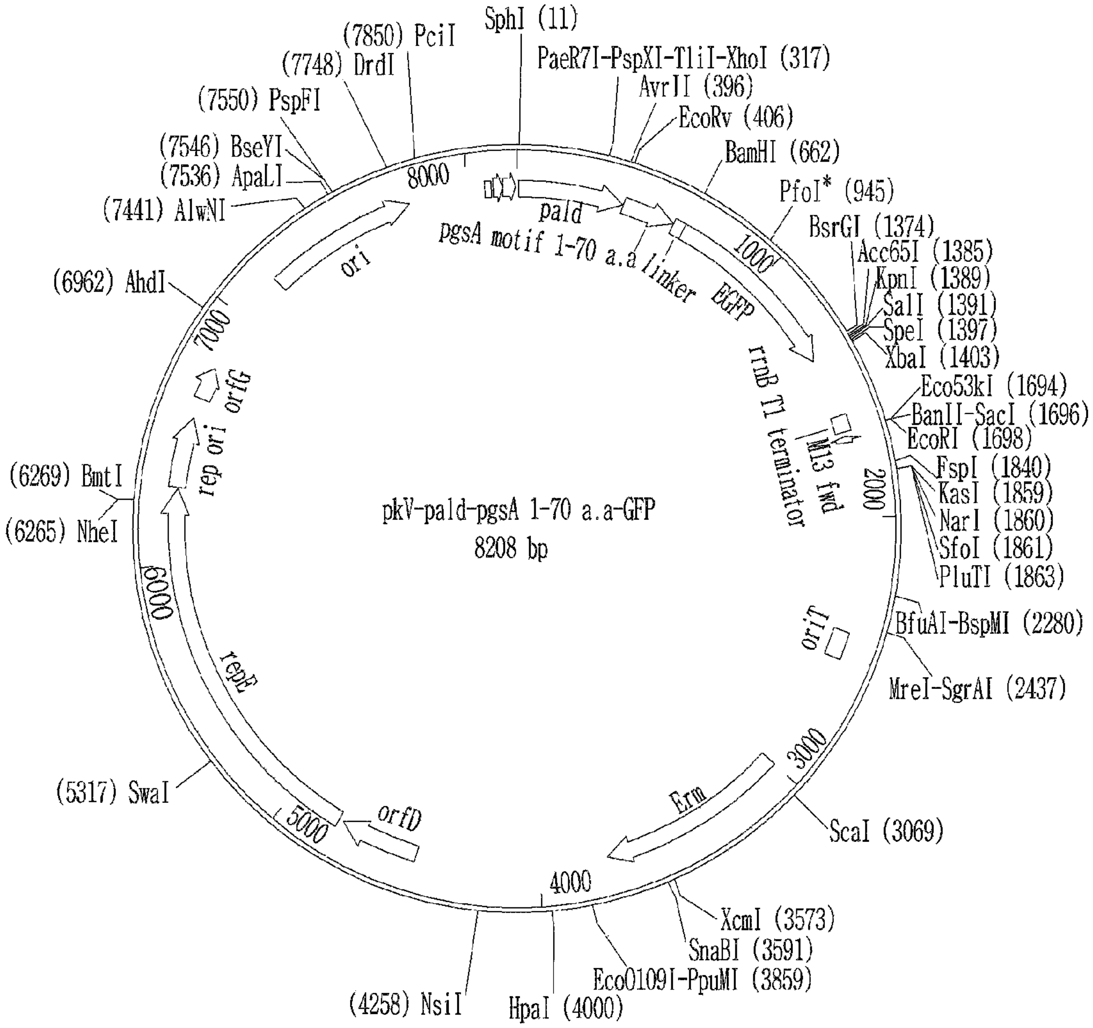
FIG. 7 shows a genetic map of the surface expression vector pKV-Pald-pgsA2 (pgsA motif 1-70 a.a)-EGFP according to the present invention, which uses *Lactobacillus casei* as a host.
Figure 8:
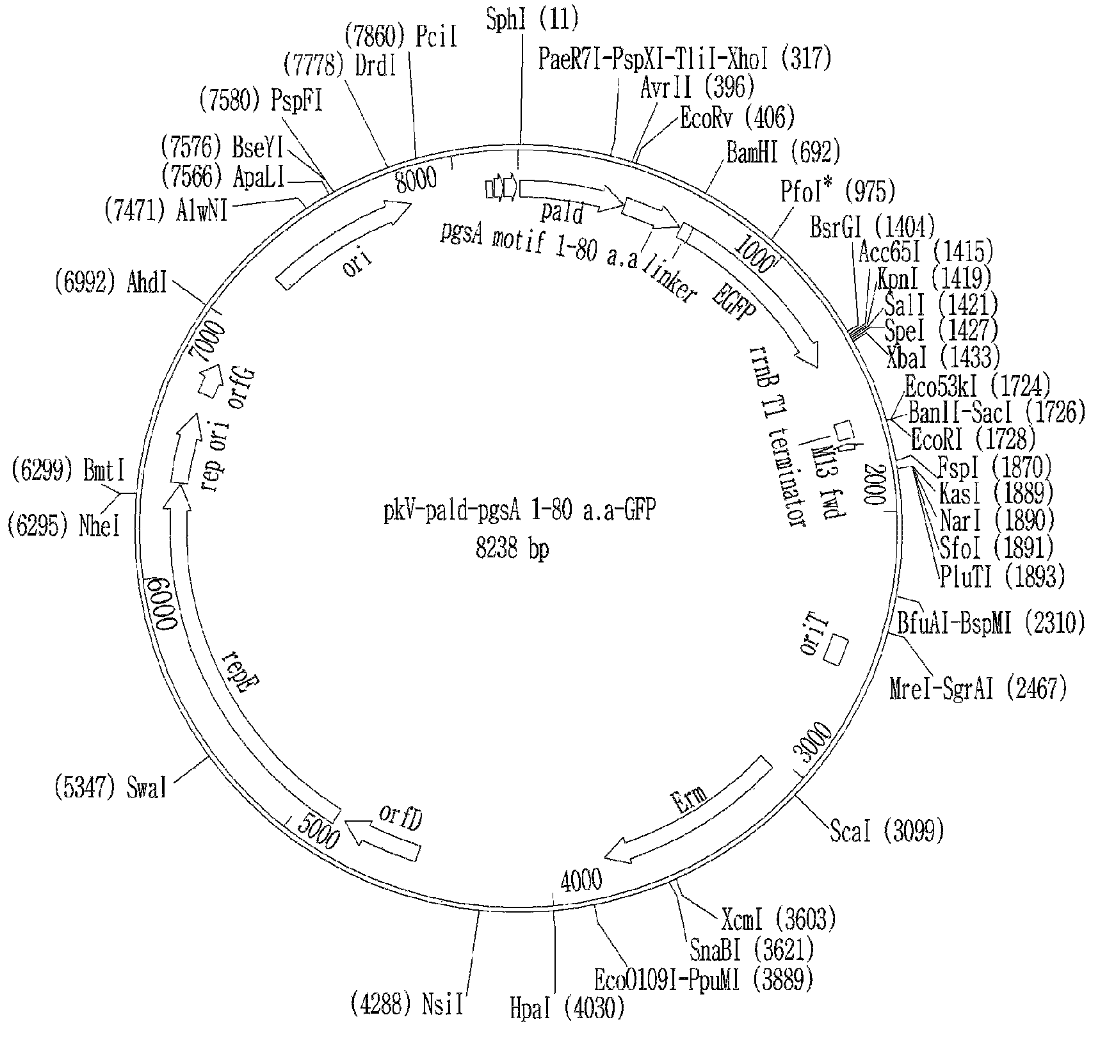
FIG. 8 shows a genetic map of the surface expression vector pKV-Pald-pgsA3 (pgsA motif 1-80 a.a)-EGFP according to the present invention, which uses *Lactobacillus casei* as a host.
Figure 9:
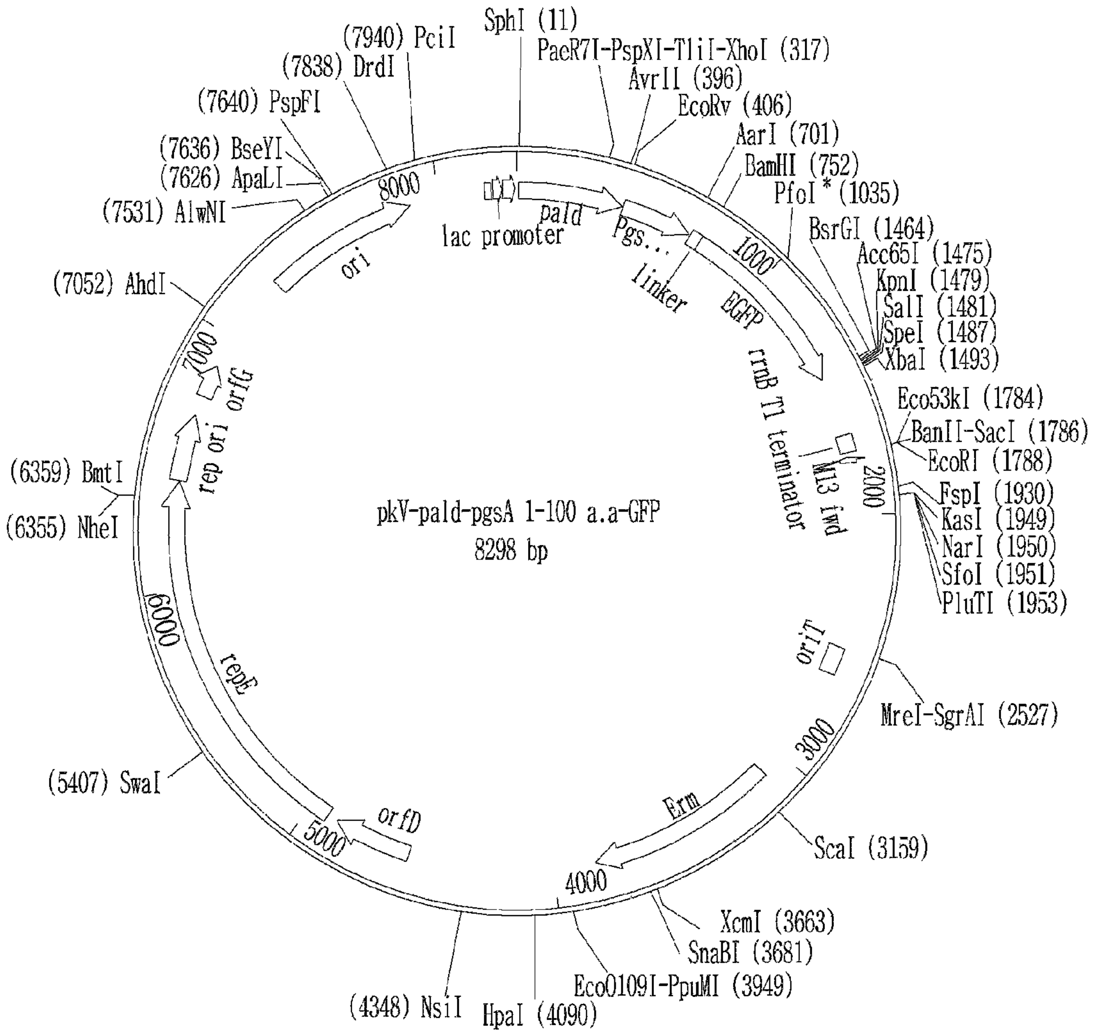
FIG. 9 shows a genetic map of the surface expression vector pKV-Pald-pgsA4 (pgsA motif 1-100 a.a)-EGFP according to the present invention, which uses *Lactobacillus casei* as a host.
Figure 10:
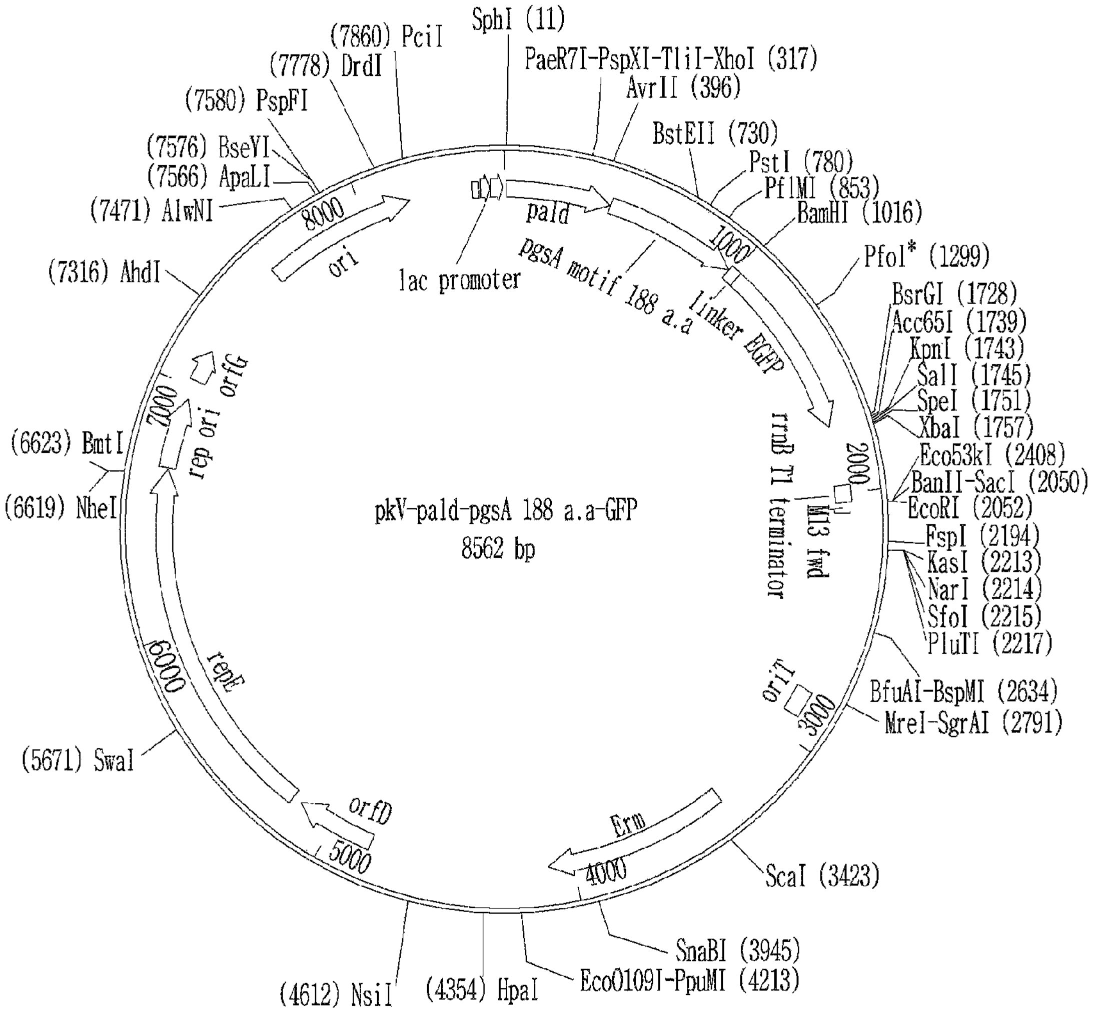
FIG. 10 shows a genetic map of the surface expression vector pKV-Pald-pgsA5 (pKV-pgsA 1-188 a.a)-EGFP according to the present invention, which uses *Lactobacillus casei* as a host.

The E7 gene-containing DNA fragment cleaved with BamHI and XbaI was ligated with the vector cleaved with the restriction enzymes, thus constructing pKV-Pald-PgsA-EGFP (FIG. 5).

Example 6: Improvement of PgsA Motif in Surface Expression Vector

In this Example, improvement of the PgsA gene fragment in the surface expression vector (pKV-Pald-PgsA-EGFP) constructed in Example 5 was performed so that the vector could exhibit a high expression level in the lactic acid bacteria host.

First, among PgsA fragments, PgsA fragments containing 1-60 a.a, 1-70 a.a, 1-80 a.a, 1-100 a.a and 1-188 a.a, respectively, were obtained by performing PCR using the surface expression vector pKV-Pald-PgsA-EGFP as a template and the following primers.

```
PgsA motif 1-60 a.a
SEQ ID NO 8:
5' TCGAGCATGCAATACCCACTTATTGCGATTTGCT 3'

SEQ ID NO 9:
5'TACGGGATCCACCAGAACCACCAGAACCACCAGAACCACCA

GAACCACCTGAGAGTACGTCGTCAGAATACGTT 3'

PgsA motif 1-70 a.a
SEQ ID NO 10:
5' TCGAGCATGCAATACCCACTTATTGCGATTTGCT3'

SEQ ID NO 11:
5'
TACGGGATCCACCAGAACCACCAGAACCACCAGAACCACCAGAACCA

CCTCCCATCATAATATCGCCTACAAAT 3'

PgsA motif 1-80 a.a
SEQ ID NO 12:
5' TCGAGCATGCAATACCCACTTATTGCGATTTGCT 3'

SEQ ID NO 13:
5'TACGGGATCCACCAGAACCACCAGAACCACCAGAACCACCAGAAC

CACCTTTTTGCTCCGTTACTTTTTCAACA 3'
```

-continued

PgsA motif 1-100 a.a
SEQ ID NO 14:
5' TCGAGCATGCAATACCCACTTATTGCGATTTGCT 3'

SEQ ID NO 15:
5'TACGGGATCCACCAGAACCACCAGAACCACCAGAACCACCAGAAC

CACCTGCTACATAATCCGAGGCTCTAAAG 3'

PgsA motif 1-188 a.a
SEQ ID NO 16:
5' TCGAGCATGCAATACCCACTTATTGCGATTTGCT 3'

SEQ ID NO 17:
5'
TACGGGATCCACCAGAACCACCAGAACCACCAGAACCACCAGAACCA

CCGACTTTCTGGTACGAAATTTTCTTT 3'

As a result, DNA fragments containing an aldolase promoter and the respective PgsA motif fragments were obtained. Each of the DNA fragments contained an SphI restriction enzyme site at the 5' end thereof and a BamHI restriction enzyme site at the 3' end thereof. Each of the obtained DNA fragments was treated with SphI and BamHI to obtain fragments. In addition, it was confirmed that the PgsA1 to PgsA5 motif fragments had the following nucleotide sequences, respectively.

PgsA 1-60 a.a Fragment Sequence (PgsA1)

PgsA 1-60 a.a fragment sequence (PgsA1)
SEQ ID NO 18:
5'ATGAAAAAAGAACTGAGCTTTCATGAAAAGCTGCTAAAGCTGACAAAA

CAGCAAAAAAAGAAAACCAATAAGCACGTATTTATTGCCATTCCGATCGT

TTTTGTCCTTATGTTCGCTTTCATGTGGGCGGGAAAAGCGGAAACGCCGA

AGGTCAAAACGTATTCTGACGACGTACTCTCA 3'

PgsA 1-70 a.a fragment sequence (PgsA2)
SEQ ID NO 19:
5'ATGAAAAAAGAACTGAGCTTTCATGAAAAGCTGCTAAAGCTGACAAAA

CAGCAAAAAAAGAAAACCAATAAGCACGTATTTATTGCCATTCCGATCGT

TTTTGTCCTTATGTTCGCTTTCATGTGGGCGGGAAAAGCGGAAACGCCGA

AGGTCAAAACGTATTCTGACGACGTACTCTCAGCCTCATTTGTAGGCGAT

ATTATGATGGGA 3'

PgsA 1-80 a.a fragment sequence (PgsA3)
SEQ ID NO 20:
5'ATGAAAAAAGAACTGAGCTTTCATGAAAAGCTGCTAAAGCTGACAAAA

CAGCAAAAAAAGAAAACCAATAAGCACGTATTTATTGCCATTCCGATCGT

TTTTGTCCTTATGTTCGCTTTCATGTGGGCGGGAAAAGCGGAAACGCCGA

AGGTCAAAACGTATTCTGACGACGTACTCTCAGCCTCATTTGTAGGCGAT

ATTATGATGGGACGCTATGTTGAAAAAGTAACGGAGCAAAAA 3'

PgsA 1-100 a.a fragment sequence (PgsA4)
SEQ ID NO 21:
5'ATGAAAAAAGAACTGAGCTTTCATGAAAAGCTGCTAAAGCTGACAAAA

CAGCAAAAAAAGAAAACCAATAAGCACGTATTTATTGCCATTCCGATCGT

TTTTGTCCTTATGTTCGCTTTCATGTGGGCGGGAAAAGCGGAAACGCCGA

AGGTCAAAACGTATTCTGACGACGTACTCTCAGCCTCATTTGTAGGCGAT

-continued

ATTATGATGGGACGCTATGTTGAAAAAGTAACGGAGCAAAAAGGGGCAGA

CAGTATTTTTCAATATGTTGAACCGATCTTTAGAGCCTCGGATTATGTAG

CA 3'

PgsA 1-188 a.a fragment sequence (PgsA5)
SEQ ID NO 22:
5'ATGAAAAAAGAACTGAGCTTTCATGAAAAGCTGCTAAAGCTGACAAAA

CAGCAAAAAAAGAAAACCAATAAGCACGTATTTATTGCCATTCCGATCGT

TTTTGTCCTTATGTTCGCTTTCATGTGGGCGGGAAAAGCGGAAACGCCGA

AGGTCAAAACGTATTCTGACGACGTACTCTCAGCCTCATTTGTAGGCGAT

ATTATGATGGGACGCTATGTTGAAAAAGTAACGGAGCAAAAAGGGGCAGA

CAGTATTTTTCAATATGTTGAACCGATCTTTAGAGCCTCGGATTATGTAG

CAGGAAACTTTGAAAACCCGGTAACCTATCAAAAGAATTATAAACAAGCA

GATAAAGAGATTCATCTGCAGACGAATAAGGAATCAGTGAAAGTCTTGAA

GGATATGAATTTCACGGTTCTCAACAGCGCCAACAACCACGCAATGGATT

ACGGCGTTCAGGGCATGAAAGATACGCTTGGAGAATTTGCGAAGCAAAAC

CTTGATATCGTTGGAGCGGGATACAGCTTAAGTGATGCGAAAAAGAAAAT

TTCGTACCAGAAAGTC 3'

The pKV-Pald-PgsA-EGFP was cleaved with SphI and BamHI to remove the aldolase promoter and the PgsA gene region and to obtain the vector region.

Each of the DNA fragments, cleaved with SphI and BamHI and containing an aldolase promoter and the respective PgsA motif fragment genes, was ligated with the vector cleaved with the same restriction enzymes, thus constructing improved vectors (FIGS. 6 to 10).

Meanwhile, among PgsA fragments, PgsA fragments containing 25-60 a.a, 25-70 a.a and 25-100 a.a, respectively, were obtained by performing PCR using the surface expression vector (pKV-Pald-PgsA-EGFP) as a template and the following primers.

PgsA motif 25-60 a.a
SEQ ID NO 23:
5' CGCTGGATATCTACATGCACGTATTTATTGCCATTCCG 3'

SEQ ID NO 24:
5'TACGGGATCCACCAGAACCACCAGAACCACCAGAACCACCAGAACCAC

CTGAGAGTACGTCGTCAGAATACGTT 3'

PgsA motif 25-70 a.a
SEQ ID NO 25:
5' CGCTGGATATCTACATGCACGTATTTATTGCCATTCCG 3'

SEQ ID NO 26:
5'TACGGGATCCACCAGAACCACCAGAACCACCAGAACCACCAGAACCAC

CTCCCATCATAATATCGCCTACAAAT 3'

PgsA motif 25-100 a.a
SEQ ID NO 27:
5' CGCTGGATATCTACATGCACGTATTTATTGCCATTCCG 3'

SEQ ID NO 28:
5'TACGGGATCCACCAGAACCACCAGAACCACCAGAACCACCAGAACCAC

CTGCTACATAATCCGAGGCTCTAAAG 3'

As a result, DNA fragments containing the respective PgsA motif fragments were obtained. Each of the fragments contained an EcoRV restriction enzyme site at the 5' end thereof and a BamHI restriction enzyme site at the 3' end thereof. Each of the obtained DNA fragments was treated with EcoRV and BamHI to obtain fragments. In addition, it was confirmed that the PgsA motif fragments have the following nucleotide sequences, respectively.

```
PgsA 25-60 a.a fragment sequence (PgsA6)
SEQ ID NO 29:
5'CACGTATTTATTGCCATTCCGATCGTTTTTGTCCTTATGTTCGCTTTC

ATGTGGGCGGGAAAAGCGGAAACGCCGAAGGTCAAAACGTATTCTGACGA

CGTACTCTCA 3'

PgsA 25-70 a.a fragment sequence (PgsA7)
SEQ ID NO 30:
5'CACGTATTTATTGCCATTCCGATCGTTTTTGTCCTTATGTTCGCTTTC

ATGTGGGCGGGAAAAGCGGAAACGCCGAAGGTCAAAACGTATTCTGACGA

CGTACTCTCAGCCTCATTTGTAGGCGATATTATGATGGGA 3

PgsA 25-100 a.a fragment sequence (PgsA8)
SEQ ID NO 31:
5'CACGTATTTATTGCCATTCCGATCGTTTTTGTCCTTATGTTCGCTTTC

ATGTGGGCGGGAAAAGCGGAAACGCCGAAGGTCAAAACGTATTCTGACGA

CGTACTCTCAGCCTCATTTGTAGGCGATATTATGATGGGACGCTATGTTG

AAAAAGTAACGGAGCAAAAAGGGGCAGACAGTATTTTTCAATATGTTGAA

CCGATCTTTAGAGCCTCGGATTATGTAGCA 3'
```

pKV-Pald-PgsA-EGFP was cleaved with EcoRV and BamHI to remove the PgsA gene region and to obtain the vector region.

Figure 11:
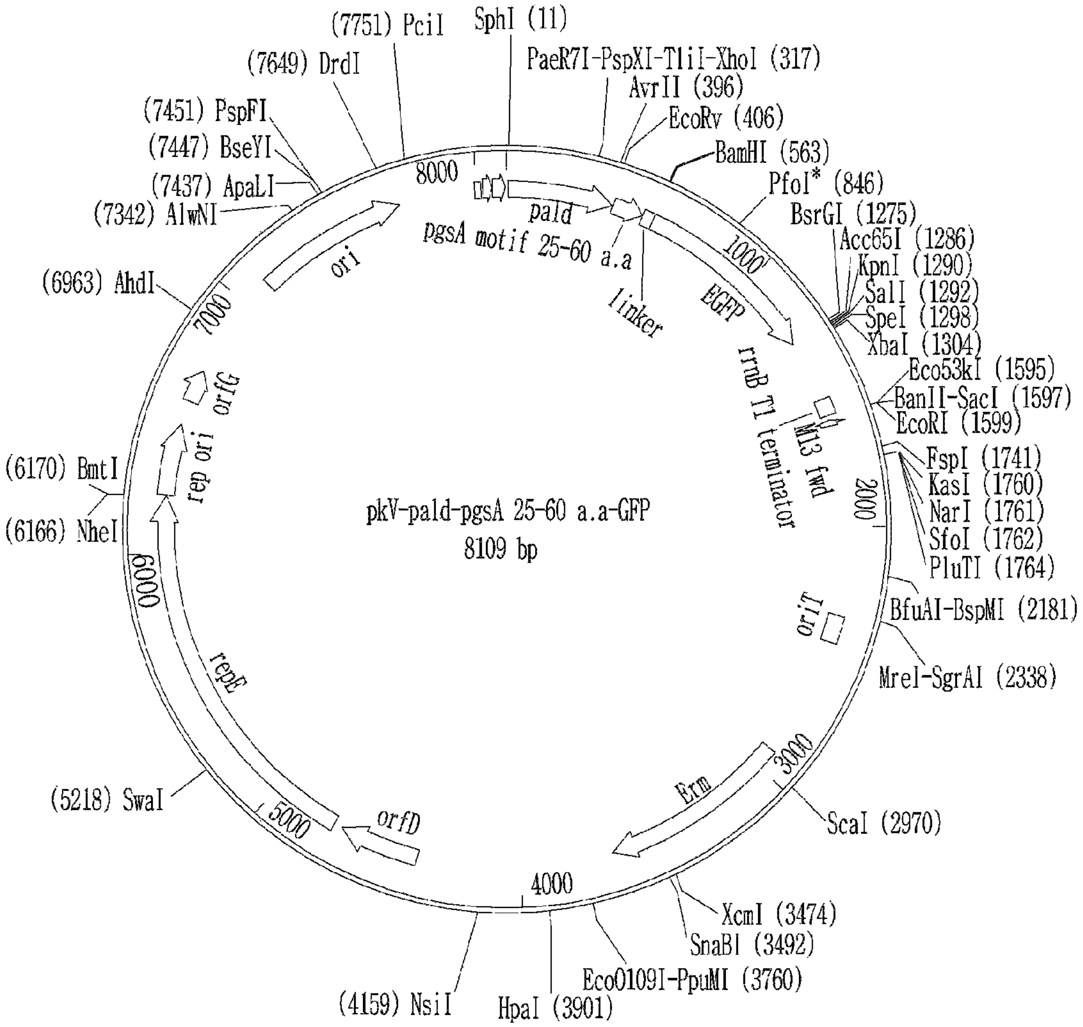
FIG. 11 shows a genetic map of the surface expression vector pKV-Pald-pgsA6 (pgsA motif 25-60 a.a)-EGFP according to the present invention, which uses *Lactobacillus casei* as a host.
Figure 12:
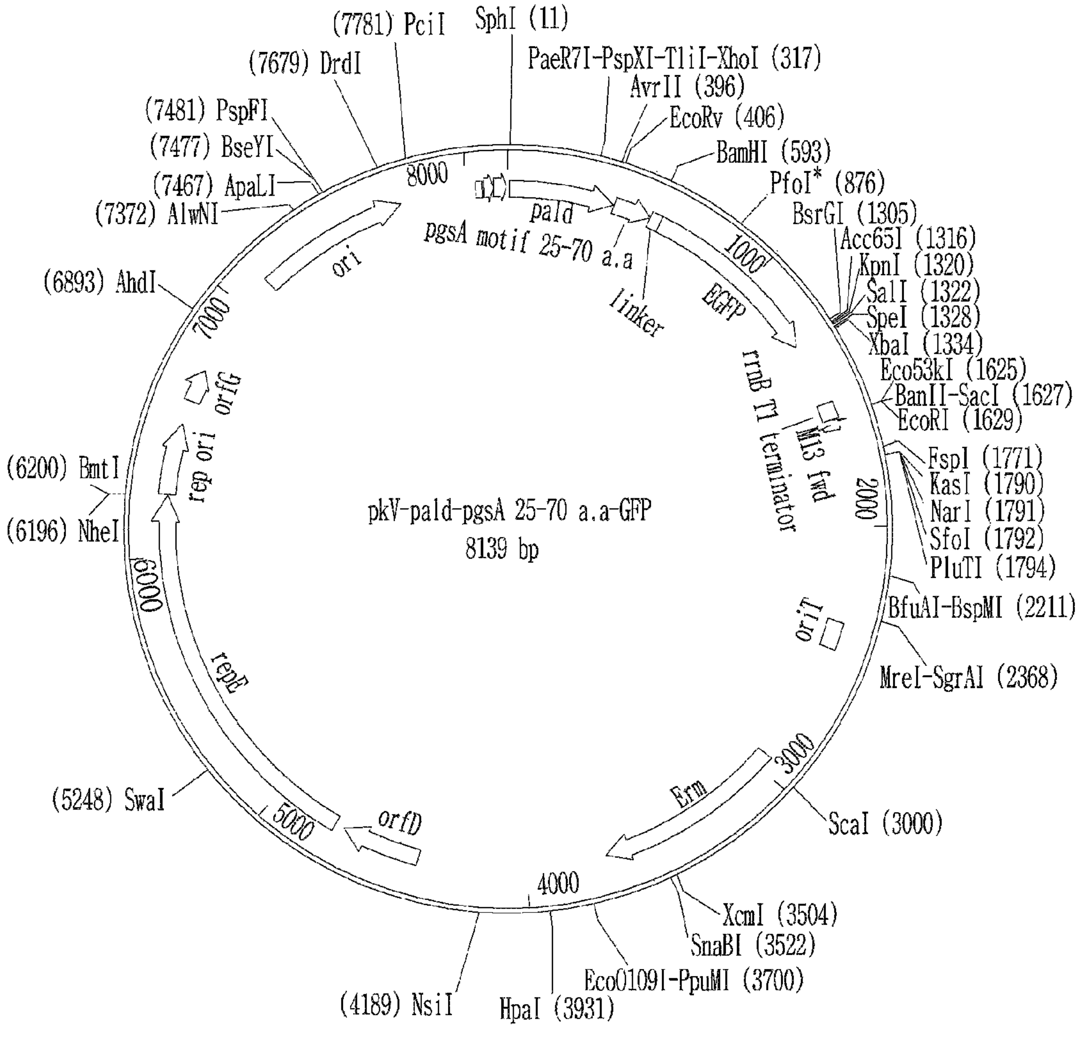
FIG. 12 shows a genetic map of the surface expression vector pKV-Pald-pgsA7 (pgsA motif 25-70 a.a)-EGFP according to the present invention, which uses *Lactobacillus casei* as a host.
Figure 13:
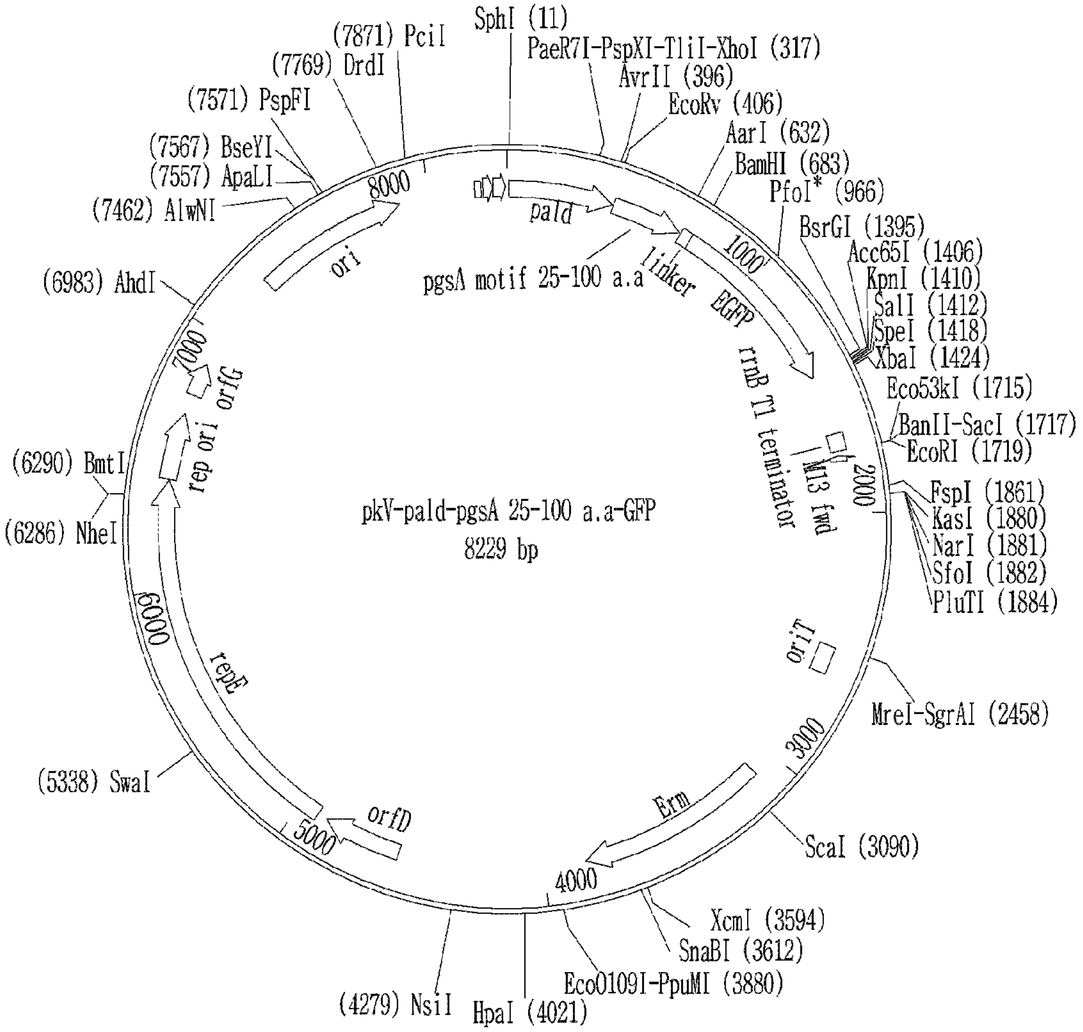
FIG. 13 shows a genetic map of the surface expression vector pKV-Pald-pgsA8 (pgsA motif 25-100 a.a)-EGFP according to the present invention, which uses *Lactobacillus casei* as a host.

Each of the DNA fragments, cleaved with EcoRV and BamHI and containing the respective PgsA motif fragment genes, was ligated with the vector cleaved with the same restriction enzymes, thus constructing improved vectors (FIGS. 11 to 13).

Example 7: Analysis of Expression on Transformants Obtained by Transformation with PgsA Motif-Improved Surface Expression Vectors In this Example, *Lactobacillus casei* was transformed with each of the PgsA motif-improved surface expression vectors constructed in Example 5, and the transformed recombinant *Lactobacillus casei* was cultured and expression of the EGFP protein thereon was analyzed. Examination was made as to whether the EGFP protein fused with any one of the improved fragments pgsA1 to pgsA8 was expressed on the transformed recombinant *Lactobacillus casei.*

The recombinant *Lactobacillus casei* transformed with each of the surface expression vectors containing each PgsA motif fragment was stationary-cultured in MRS medium (*Lactobacillus* MRS, Becton Dickinson and Company Sparks, USA) at 30° C. to induce surface expression of the EGFP protein fused with the C-terminus of any one of the gene fragments pgsA1 to pgsA8 involved in the synthesis of poly-gamma-glutamate.

Expression of the fusion protein was analyzed by subjecting the cultured *Lactobacillus casei* whole cells to SDS-polyamide gel electrophoresis and to Western blotting using a specific antibody against EGFP.

Specifically, the recombinant *Lactobacillus casei* whole cells on which protein expression was induced were denatured with proteins obtained at the same cell concentration to prepare a sample. The sample was analyzed by SDS-polyacrylamide gel electrophoresis, and then the fractionated proteins were transferred to a PVDF (polyvinylidene-difluoride) membrane (Bio-Rad). The PVDF membrane having the proteins transferred thereto was blocked by shaking in blocking buffer (50 mM Tris-HCl, 5% skim milk, pH 8.0) for 1 hour, and then incubated for 1 hour with a 1:1,000 dilution of an anti-rabbit polyclonal primary antibody against EGFP in blocking buffer. After completion of the incubation, the membrane was washed with buffer and incubated for 1 hour with a 1:10,000 dilution of HRP (horseradish peroxidase)-conjugated anti-rabbit secondary antibody in blocking solution. After completion of the incubation, the membrane was washed with buffer, and the washed membrane was color-developed with a substrate (Lumigen PS-3 acridan, $H_2O_2$) for about 2 minutes. Then, specific binding between the specific antibody against EGFP and the fusion protein was visualized by a CCD camera (FIG. 14).

Figure 14:
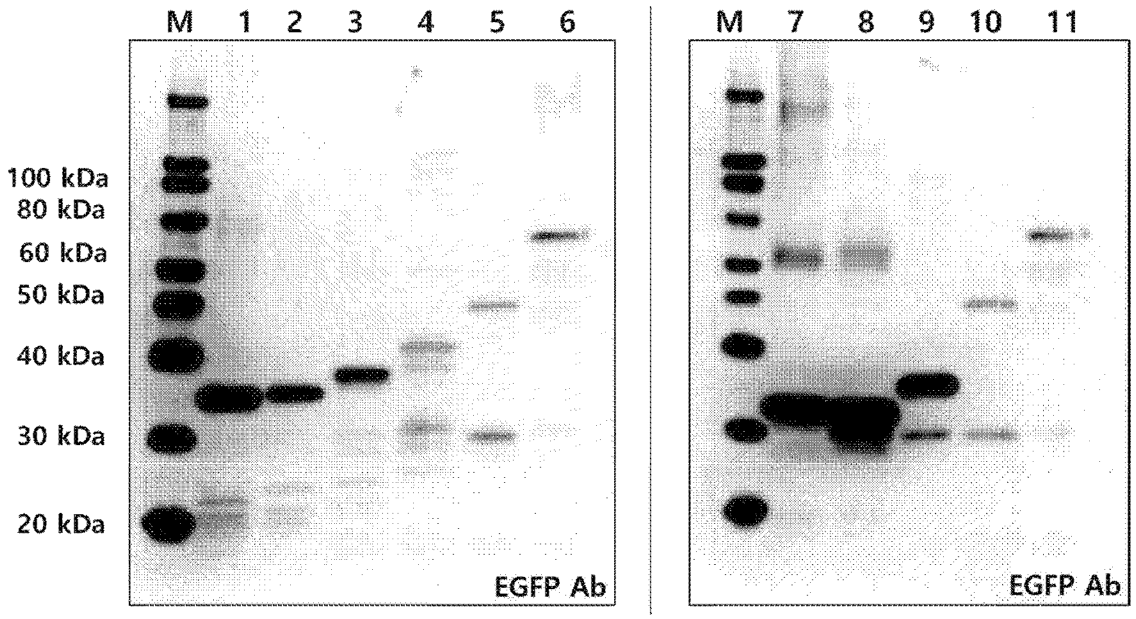
FIG. 14 depicts Western blot images showing the surface expression of EGFP protein in *Lactobacillus casei* transformed with each of the surface expression vectors pKV-Pald-pgsA1 to pKV-Pald-pgsA8 of the present invention.

FIG. 14 shows expression patterns (lanes 6 and 11) in *Lactobacillus casei* depending on the recombinant expression vector pKV-Pald-pgsA containing the non-improved pgsA as a control for comparison with the present invention, and expression patterns (lanes 1 to 5 and lanes 7 to 10) in *Lactobacillus casei* depending on the recombinant expression vectors pKV-Pald-pgsA1 to pgsA8 containing the improved pgsA1 to pgsA8 according to the present invention.

Specifically, in FIG. 14, lane 1 represents protein expression on the recombinant *Lactobacillus casei* transformed with EGFP fused with PgsA motif 1-60 a.a; lane 2 represents protein expression on the recombinant *Lactobacillus casei* transformed with EGFP fused with PgsA motif 1-70 a.a; lane 3 represents protein expression on the recombinant *Lactobacillus casei* transformed with EGFP fused with PgsA motif 1-80 a.a; and lane 4 represents protein expression on the recombinant *Lactobacillus casei* transformed with EGFP fused with PgsA motif 1-100 a.a. Lane 5 represents protein expression on the recombinant *Lactobacillus casei* transformed with EGFP fused with PgsA motif 1-188 a.a. Lane 6 represents protein expression on the recombinant *Lactobacillus casei* transformed with pKV-Pald-PgsA-EGFP.

In addition, in FIG. 14, lane 7 represents protein expression on the recombinant *Lactobacillus casei* transformed with EGFP fused with PgsA motif 26-50 a.a; lane 8 represents protein expression on the recombinant *Lactobacillus casei* transformed with EGFP fused with PgsA motif 25-70 a.a; and lane 9 represents protein expression on the recombinant *Lactobacillus casei* transformed with EGFP fused with PgsA motif 25-100 a.a. Lane 10 represents protein expression on the recombinant *Lactobacillus casei* transformed with EGFP fused with PgsA motif 1-188 a.a. Lane 11 represents protein expression on the recombinant *Lactobacillus casei* transformed with pKV-Pald-PgsA-EGFP.

It was confirmed that the expression of the EGFP fusion protein comprising the improved PgsA motif fragment was stronger than the expression of the EGFP fusion protein by the non-improved surface expression vector pKV-Pald-pgsA-EGFP.

INDUSTRIAL APPLICABILITY

The present invention relates to a novel vector which effectively expresses a foreign protein on the microbial surface using a galactose mutarotase gene promoter derived from *Lactobacillus casei* and an outer membrane protein which is derived from a *Bacillus* sp. strain and involved in the synthesis of poly-gamma-glutamate. Since the vector contains the gene which anchors the target protein to the microbial surface, the target protein may be effectively expressed on the cell surface in a transformant obtained using the vector, and thus lactic acid bacteria may be used as a vaccine vehicle. In addition, the surface expression vector for expressing a target protein according to the present invention may stably express the target protein. The surface expression vector for expressing a target protein according to the present invention may express the target protein on the surface of a recombinant microorganism while constitutively expressing the target protein, and thus may be effectively used for the production of an antigen for producing a necessary vaccine. Therefore, the present invention is industrially applicable.

[Sequence List Text]

SEQ ID NO: 1
5' ttgaattggt ttcttacgat ggtaagacca acgaaactgg tacagctgca tgggctaaag ctaagcctga
aaaggtcatc aagatcacca aggaattcag caagccgcaa tacaatgttt ctgttttgaa gcttgaagtt
ccagttgatc aaaagtttgt tgaaggctac accgatgacg gcgttacccc tgtttacagc aaggaagaag
ccgctaagta ttacaaggaa cagtcagatg caacggatct cccattcatc ttcctgtccg ctggtgtcac
caacgaattg ttccttgaag aactcaagtt tgctaagcaa gcaggttcag cctttaatgg tgttctctgt
ggccgtgcaa cttggaagcc gggtgttaag ccatatgctg ctgaaggcga agctgctggt aagaagtggc
tgcagaccga aggcaaggct aacattgatc gtttgaacaa ggtgcttgca gaaactgcaa ccccttggac
tgacaaagtt gaaggttaat ctttaaccat agttgcaaga aaggaccgat tatgatgatc ggttcttttt
ttatgactgc ggacatgttt ttgtgaccac tgcaaacatc aaatgaagt tcgaaaaact tgctaacaat
cattacaggt cagtgatcca gtggtagact gtattgaat gcgttttcgt ctattaggag gtaattcaac 3'

SEQ ID NO: 2
5' tacggcatgc ttgaattggt ttcttacgat 3'

SEQ ID NO: 3
5' tacgctcgag gttgaattac ctcctaatag 3'

SEQ ID NO: 4
5' tggtggatcc gtgagcaagg gcgaggagct g 3'

SEQ ID NO: 5
5' tgactctaga actagtgtcg acggtacctt acttgtacag ctcgtcc 3'

SEQ ID NO: 6
5'tggtggatcc gtgagcaagg gcgaggagct g 3'

SEQ ID NO: 7
5' tgactctaga actagtgtcg acggtacctt acttgtacag ctcgtcc 3'

SEQ ID NO: 8
5' tcgagcatgc aatacccact tattgcgatt tgct 3'

SEQ ID NO: 9
5' tacgggatcc accagaacca ccagaaccac cagaaccacc agaaccacct gagagtacgt cgtcagaata
cgtt 3'

SEQ ID NO: 10
5' tcgagcatgc aatacccact tattgcgatt tgct 3'

SEQ ID NO: 11
5' tacgggatcc accagaacca ccagaaccac cagaaccacc agaaccacct cccatcataa tatcgcctac
aaat 3'

SEQ ID NO: 12
5' tcgagcatgc aatacccact tattgcgatt tgct 3'

SEQ ID NO: 13
5' tacgggatcc accagaacca ccagaaccac cagaaccacc agaaccacct ttttgctccg ttactttttc
aaca 3'

SEQ ID NO: 14
5' tcgagcatgc aatacccact tattgcgatt tgct 3'

SEQ ID NO: 15
5' tacgggatcc accagaacca ccagaaccac cagaaccacc agaaccacct gctacataat ccgaggctct
aaag 3'

SEQ ID NO: 16
5' tcgagcatgc aatacccact tattgcgatt tgct 3'

SEQ ID NO: 17
5' tacgggatcc accagaacca ccagaaccac cagaaccacc agaaccaccg actttctggt acgaaatttt
cttt 3'

SEQ ID NO: 18
5' atgaaaaaag aactgagctt tcatgaaaag ctgctaaagc tgacaaaaca gcaaaaaaag aaaaccaata
agcacgtatt tattgccatt ccgatcgttt ttgtccttat gttcgctttc atgtgggcgg gaaaagcgga
aacgccgaag gtcaaaacgt attctgacga cgtactctca 3'

-continued

| [Sequence List Text] |
|---|
| SEQ ID NO: 19<br>5' atgaaaaaag aactgagctt tcatgaaaag ctgctaaagc tgacaaaaca gcaaaaaaag aaaaccaata agcacgtatt tattgccatt ccgatcgttt ttgtccttat gttcgctttc atgtgggcgg gaaaagcgga aacgccgaag gtcaaaacgt attctgacga cgtactctca gcctcatttg taggcgatat tatgatggga 3' |
| SEQ ID NO: 20<br>5' atgaaaaaag aactgagctt tcatgaaaag ctgctaaagc tgacaaaaca gcaaaaaaag aaaaccaata agcacgtatt tattgccatt ccgatcgttt ttgtccttat gttcgctttc atgtgggcgg gaaaagcgga aacgccgaag gtcaaaacgt attctgacga cgtactctca gcctcatttg taggcgatat tatgatggga cgctatgttg aaaaagtaac ggagcaaaaa 3' |
| SEQ ID NO: 21<br>5' atgaaaaaag aactgagctt tcatgaaaag ctgctaaagc tgacaaaaca gcaaaaaaag aaaaccaata agcacgtatt tattgccatt ccgatcgttt ttgtccttat gttcgctttc atgtgggcgg gaaaagcgga aacgccgaag gtcaaaacgt attctgacga cgtactctca gcctcatttg taggcgatat tatgatggga cgctatgttg aaaaagtaac ggagcaaaaa ggggcagaca gtatttttca atatgttgaa ccgatcttta gagcctcgga ttatgtagca 3' |
| SEQ ID NO: 22<br>5' atgaaaaaag aactgagctt tcatgaaaag ctgctaaagc tgacaaaaca gcaaaaaaag aaaaccaata agcacgtatt tattgccatt ccgatcgttt ttgtccttat gttcgctttc atgtgggcgg gaaaagcgga aacgccgaag gtcaaaacgt attctgacga cgtactctca gcctcatttg taggcgatat tatgatggga cgctatgttg aaaaagtaac ggagcaaaaa ggggcagaca gtatttttca atatgttgaa ccgatcttta gagcctcgga ttatgtagca ggaaactttg aaaacccggt aacctatcaa aagaattata aacaagcaga taaagagatt catctgcaga cgaataagga atcagtgaaa gtcttgaagg atatgaattt cacggttctc aacagcgcca acaaccacgc aatggattac ggcgttcagg gcatgaaaga tacgcttgga gaatttgcga agcaaaacct tgatatcgtt ggagcgggat acagcttaag tgatgcgaaa aagaaaattt cgtaccagaa agtc 3' |
| SEQ ID NO: 23<br>5' cgctggatat ctacatgcac gtatttattg ccattccg 3' |
| SEQ ID NO: 24<br>5' tacgggatcc accagaacca ccagaaccac cagaaccacc agaaccacct gagagtacgt cgtcagaata cgtt 3' |
| SEQ ID NO: 25<br>5' cgctggatat ctacatgcac gtatttattg ccattccg 3' |
| SEQ ID NO: 26<br>5' tacgggatcc accagaacca ccagaaccac cagaaccacc agaaccacct cccatcataa tatcgcctac aaat 3' |
| SEQ ID NO: 27<br>5' cgctggatat ctacatgcac gtatttattg ccattccg 3' |
| SEQ ID NO: 28<br>5' tacgggatcc accagaacca ccagaaccac cagaaccacc agaaccacct gctacataat ccgaggctct aaag 3' |
| SEQ ID NO: 29<br>5' cacgtattta ttgccattcc gatcgttttt gtccttatgt tcgctttcat gtgggcggga aaagcggaaa cgccgaaggt caaaacgtat tctgacgacg tactctca 3' |
| SEQ ID NO: 30<br>5' cacgtattta ttgccattcc gatcgttttt gtccttatgt tcgctttcat gtgggcggga aaagcggaaa cgccgaaggt caaaacgtat tctgacgacg tactctcagc ctcatttgta ggcgatatta tgatgggga 3' |
| SEQ ID NO: 31<br>5' cacgtattta ttgccattcc gatcgttttt gtccttatgt tcgctttcat gtgggcggga aaagcggaaa cgccgaaggt caaaacgtat tctgacgacg tactctcagc ctcatttgta ggcgatatta tgatgggacg ctatgttgaa aaagtaacgg agcaaaaagg ggcagacagt atttttcaat atgttgaacc gatctttaga gcctcggatt atgtagca 3' |

The invention claimed is:

1. A surface expression vector for expressing target proteins, the surface expression vector comprising:

a promoter of a galactose mutarotase gene derived from *Lactobacillus casei;* a gene encoding a poly-gamma-glutamate synthetase complex for surface anchoring; and a gene encoding the target protein, wherein the promoter consists of the nucleotide sequence of SEQ ID NO: 1, wherein the gene encoding the poly-gamma-glutamate synthetase complex, and the gene encoding the target protein are linked to one another, wherein the gene encoding the poly-gamma-glutamate synthetase complex is pgsA and includes the nucleotide sequence of any one of SEQ ID NOs: 18 to 20 and 29 to 31.

2. The microbial surface expression vector of claim 1, wherein the target protein is an antigen.

3. The microbial surface expression vector of claim 1, wherein the gene pgsA is derived from a *Bacillus* sp. strain that produces poly-gamma-glutamate.

4. The microbial surface expression vector of claim 1, wherein a linker is inserted into an end of the gene pgsA, and the gene encoding the target protein is inserted into the inserted linker.

5. The microbial surface expression vector of claim 1, wherein the vector is applied to Gram-negative or Gram-positive bacteria.

6. A microorganism transformed with the surface expression vector of claim 1.

7. The microorganism of claim 6, wherein a microorganism used for the transformation is a microorganism modified so that it does not produce intracellular or extracellular proteases, which are involved in degradation of the expressed target protein, in order to favor cell surface expression of the target proteins.

8. The microorganism of claim 6, which is lactic acid bacteria.

9. A method for producing a microbial vaccine, the method comprising steps of:

(a) expressing an antigen on a microbial surface by culturing a microorganism transformed with the microbial surface expression vector of claim 1; and (b) recovering the microorganism having the antigen expressed on the surface thereof.

10. The method of claim 9, wherein the microorganism is lactic acid bacteria.

11. A method for cell surface expression of a target protein, the method comprising steps of: expressing the target protein on a cell surface by culturing the transformed microorganism of claim 6; and recovering cells having the target proteins expressed on the surface thereof.

12. The method of claim 11, wherein the target protein is any one selected from the group consisting of hormones, hormone analogs, enzymes, enzyme inhibitors, signaling proteins or fragments thereof, antibodies or fragments thereof, single chain antibodies, binding proteins, binding domains, peptides, antigens, adhesion proteins, structural proteins, regulatory proteins, toxin proteins, cytokines, transcription regulatory factors, coagulation factors, and plant biodefense-inducing proteins.

13. A method of inducing humoral immunity or cellular immunity by administering cells, produced by the method of claim 12 and having an antigen expressed on a surface thereof, to vertebrates other than humans.

14. A method of expressing a target protein on a surface of a Gram-negative or Gram-positive host cell, the method comprising steps of:

(a) constructing a recombinant vector by inserting a gene encoding the target protein into the microbial surface expression vector of claim 5;

(b) transforming the Gram-negative or Gram-positive host cell with the recombinant vector, and (c) expressing the target protein on the surface of the Gram-negative or Gram-positive host cell by culturing the transformed host cell.

* * * * *

SEQUENCE LISTING

<160> NUMBER OF SEQ ID NOS: 31

<210> SEQ ID NO 1
<211> LENGTH: 700
<212> TYPE: DNA
<213> ORGANISM: Lactobacillus casei -continued

<400> SEQUENCE: 1
ttgaattggt ttcttacgat ggtaagacca acgaaactgg tacagctgca tgggctaaag 60
ctaagcctga aaaggtcatc aagatcacca aggaattcag caagccgcaa tacaatgttt 120
ctgttttgaa gcttgaagtt ccagttgatc aaaagtttgt tgaaggctac accgatgacg 180
gcgttacccc tgtttacagc aaggaagaag ccgctaagta ttacaaggaa cagtcagatg 240
caacggatct cccattcatc ttcctgtccg ctggtgtcac caacgaattg ttccttgaag 300
aactcaagtt tgctaagcaa gcaggttcag cctttaatgg tgttctctgt ggccgtgcaa 360
cttggaagcc gggtgttaag ccatatgctg ctgaaggcga agctgctggt aagaagtggc 420
tgcagaccga aggcaaggct aacattgatc gtttgaacaa ggtgcttgca gaaactgcaa 480
ccccttggac tgacaaagtt gaaggttaat ctttaaccat agttgcaaga aaggaccgat 540
tatgatgatc ggttcttttt ttatgactgc ggacatgttt ttgtgaccac tgcaaacatc 600
aaaatgaagt tcgaaaaact tgctaacaat cattacaggt cagtgatcca gtggtagact 660
ggtattgaat gcgttttcgt ctattaggag gtaattcaac 700

<210> SEQ ID NO 2
<211> LENGTH: 30
<212> TYPE: DNA
<213> ORGANISM: Artificial Sequence
<220> FEATURE:
<223> OTHER INFORMATION: Forward primer

<400> SEQUENCE: 2
tacggcatgc ttgaattggt ttcttacgat 30

<210> SEQ ID NO 3
<211> LENGTH: 30
<212> TYPE: DNA
<213> ORGANISM: Artificial Sequence
<220> FEATURE:
<223> OTHER INFORMATION: Reverse primer

<400> SEQUENCE: 3
tacgctcgag gttgaattac ctcctaatag 30

<210> SEQ ID NO 4
<211> LENGTH: 31
<212> TYPE: DNA
<213> ORGANISM: Artificial Sequence
<220> FEATURE:
<223> OTHER INFORMATION: Forward primer

<400> SEQUENCE: 4
tggtggatcc gtgagcaagg gcgaggagct g 31

<210> SEQ ID NO 5
<211> LENGTH: 47
<212> TYPE: DNA
<213> ORGANISM: Artificial Sequence
<220> FEATURE:
<223> OTHER INFORMATION: Reverse primer

<400> SEQUENCE: 5
tgactctaga actagtgtcg acggtacctt acttgtacag ctcgtcc 47

<210> SEQ ID NO 6
<211> LENGTH: 31
<212> TYPE: DNA

-continued

<213> ORGANISM: Artificial Sequence
<220> FEATURE:
<223> OTHER INFORMATION: PCR primer

<400> SEQUENCE: 6
tggtggatcc gtgagcaagg gcgaggagct g 31

<210> SEQ ID NO 7
<211> LENGTH: 47
<212> TYPE: DNA
<213> ORGANISM: Artificial Sequence
<220> FEATURE:
<223> OTHER INFORMATION: PCR primer

<400> SEQUENCE: 7
tgactctaga actagtgtcg acggtacctt acttgtacag ctcgtcc 47

<210> SEQ ID NO 8
<211> LENGTH: 34
<212> TYPE: DNA
<213> ORGANISM: Artificial Sequence
<220> FEATURE:
<223> OTHER INFORMATION: PCR primer

<400> SEQUENCE: 8
tcgagcatgc aatacccact tattgcgatt tgct 34

<210> SEQ ID NO 9
<211> LENGTH: 74
<212> TYPE: DNA
<213> ORGANISM: Artificial Sequence
<220> FEATURE:
<223> OTHER INFORMATION: PCR primer

<400> SEQUENCE: 9
tacgggatcc accagaacca ccagaaccac cagaaccacc agaaccacct gagagtacgt 60
cgtcagaata cgtt 74

<210> SEQ ID NO 10
<211> LENGTH: 34
<212> TYPE: DNA
<213> ORGANISM: Artificial Sequence
<220> FEATURE:
<223> OTHER INFORMATION: PCR primer

<400> SEQUENCE: 10
tcgagcatgc aatacccact tattgcgatt tgct 34

<210> SEQ ID NO 11
<211> LENGTH: 74
<212> TYPE: DNA
<213> ORGANISM: Artificial Sequence
<220> FEATURE:
<223> OTHER INFORMATION: PCR primer

<400> SEQUENCE: 11
tacgggatcc accagaacca ccagaaccac cagaaccacc agaaccacct cccatcataa 60
tatcgcctac aaat 74

<210> SEQ ID NO 12
<211> LENGTH: 34
<212> TYPE: DNA
<213> ORGANISM: Artificial Sequence
<220> FEATURE:
<223> OTHER INFORMATION: PCR primer -continued

<400> SEQUENCE: 12
tcgagcatgc aatacccact tattgcgatt tgct 34

<210> SEQ ID NO 13
<211> LENGTH: 74
<212> TYPE: DNA
<213> ORGANISM: Artificial Sequence
<220> FEATURE:
<223> OTHER INFORMATION: PCR primer

<400> SEQUENCE: 13
tacgggatcc accagaacca ccagaaccac cagaaccacc agaaccacct ttttgctccg 60
ttactttttc aaca 74

<210> SEQ ID NO 14
<211> LENGTH: 34
<212> TYPE: DNA
<213> ORGANISM: Artificial Sequence
<220> FEATURE:
<223> OTHER INFORMATION: PCR primer

<400> SEQUENCE: 14
tcgagcatgc aatacccact tattgcgatt tgct 34

<210> SEQ ID NO 15
<211> LENGTH: 74
<212> TYPE: DNA
<213> ORGANISM: Artificial Sequence
<220> FEATURE:
<223> OTHER INFORMATION: PCR primer

<400> SEQUENCE: 15
tacgggatcc accagaacca ccagaaccac cagaaccacc agaaccacct gctacataat 60
ccgaggctct aaag 74

<210> SEQ ID NO 16
<211> LENGTH: 34
<212> TYPE: DNA
<213> ORGANISM: Artificial Sequence
<220> FEATURE:
<223> OTHER INFORMATION: PCR primer

<400> SEQUENCE: 16
tcgagcatgc aatacccact tattgcgatt tgct 34

<210> SEQ ID NO 17
<211> LENGTH: 74
<212> TYPE: DNA
<213> ORGANISM: Artificial Sequence
<220> FEATURE:
<223> OTHER INFORMATION: PCR primer

<400> SEQUENCE: 17
tacgggatcc accagaacca ccagaaccac cagaaccacc agaaccaccg actttctggt 60
acgaaatttt cttt 74

<210> SEQ ID NO 18
<211> LENGTH: 180
<212> TYPE: DNA
<213> ORGANISM: Artificial Sequence
<220> FEATURE:
<223> OTHER INFORMATION: pgsA1

<400> SEQUENCE: 18

```
atgaaaaaag aactgagctt tcatgaaaag ctgctaaagc tgacaaaaca gcaaaaaaag     60
aaaaccaata agcacgtatt tattgccatt ccgatcgttt ttgtccttat gttcgctttc    120
atgtgggcgg gaaaagcgga aacgccgaag gtcaaaacgt attctgacga cgtactctca    180
```

<210> SEQ ID NO 19
<211> LENGTH: 210
<212> TYPE: DNA
<213> ORGANISM: Artificial Sequence
<220> FEATURE:
<223> OTHER INFORMATION: pgsA2

<400> SEQUENCE: 19

```
atgaaaaaag aactgagctt tcatgaaaag ctgctaaagc tgacaaaaca gcaaaaaaag     60
aaaaccaata agcacgtatt tattgccatt ccgatcgttt ttgtccttat gttcgctttc    120
atgtgggcgg gaaaagcgga aacgccgaag gtcaaaacgt attctgacga cgtactctca    180
gcctcatttg taggcgatat tatgatggga                                     210
```

<210> SEQ ID NO 20
<211> LENGTH: 240
<212> TYPE: DNA
<213> ORGANISM: Artificial Sequence
<220> FEATURE:
<223> OTHER INFORMATION: pgsA3

<400> SEQUENCE: 20

```
atgaaaaaag aactgagctt tcatgaaaag ctgctaaagc tgacaaaaca gcaaaaaaag     60
aaaaccaata agcacgtatt tattgccatt ccgatcgttt ttgtccttat gttcgctttc    120
atgtgggcgg gaaaagcgga aacgccgaag gtcaaaacgt attctgacga cgtactctca    180
gcctcatttg taggcgatat tatgatggga cgctatgttg aaaaagtaac ggagcaaaaa    240
```

<210> SEQ ID NO 21
<211> LENGTH: 300
<212> TYPE: DNA
<213> ORGANISM: Artificial Sequence
<220> FEATURE:
<223> OTHER INFORMATION: pgsA4

<400> SEQUENCE: 21

```
atgaaaaaag aactgagctt tcatgaaaag ctgctaaagc tgacaaaaca gcaaaaaaag     60
aaaaccaata agcacgtatt tattgccatt ccgatcgttt ttgtccttat gttcgctttc    120
atgtgggcgg gaaaagcgga aacgccgaag gtcaaaacgt attctgacga cgtactctca    180
gcctcatttg taggcgatat tatgatggga cgctatgttg aaaaagtaac ggagcaaaaa    240
ggggcagaca gtatttttca atatgttgaa ccgatcttta gagcctcgga ttatgtagca    300
```

<210> SEQ ID NO 22
<211> LENGTH: 564
<212> TYPE: DNA
<213> ORGANISM: Artificial Sequence
<220> FEATURE:
<223> OTHER INFORMATION: pgsA5

<400> SEQUENCE: 22

```
atgaaaaaag aactgagctt tcatgaaaag ctgctaaagc tgacaaaaca gcaaaaaaag     60
aaaaccaata agcacgtatt tattgccatt ccgatcgttt ttgtccttat gttcgctttc    120
atgtgggcgg gaaaagcgga aacgccgaag gtcaaaacgt attctgacga cgtactctca    180
```

gcctcatttg taggcgatat tatgatggga cgctatgttg aaaaagtaac ggagcaaaaa 240
ggggcagaca gtatttttca atatgttgaa ccgatcttta gagcctcgga ttatgtagca 300
ggaaactttg aaaacccggt aacctatcaa aagaattata aacaagcaga taaagagatt 360
catctgcaga cgaataagga atcagtgaaa gtcttgaagg atatgaattt cacggttctc 420
aacagcgcca acaaccacgc aatggattac ggcgttcagg gcatgaaaga tacgcttgga 480
gaatttgcga agcaaaacct tgatatcgtt ggagcgggat acagcttaag tgatgcgaaa 540
aagaaaattt cgtaccagaa agtc 564

<210> SEQ ID NO 23
<211> LENGTH: 38
<212> TYPE: DNA
<213> ORGANISM: Artificial Sequence
<220> FEATURE:
<223> OTHER INFORMATION: PCR primer

<400> SEQUENCE: 23
cgctggatat ctacatgcac gtatttattg ccattccg 38

<210> SEQ ID NO 24
<211> LENGTH: 74
<212> TYPE: DNA
<213> ORGANISM: Artificial Sequence
<220> FEATURE:
<223> OTHER INFORMATION: PCR primer

<400> SEQUENCE: 24
tacgggatcc accagaacca ccagaaccac cagaaccacc agaaccacct gagagtacgt 60
cgtcagaata cgtt 74

<210> SEQ ID NO 25
<211> LENGTH: 38
<212> TYPE: DNA
<213> ORGANISM: Artificial Sequence
<220> FEATURE:
<223> OTHER INFORMATION: PCR primer

<400> SEQUENCE: 25
cgctggatat ctacatgcac gtatttattg ccattccg 38

<210> SEQ ID NO 26
<211> LENGTH: 74
<212> TYPE: DNA
<213> ORGANISM: Artificial Sequence
<220> FEATURE:
<223> OTHER INFORMATION: PCR primer

<400> SEQUENCE: 26
tacgggatcc accagaacca ccagaaccac cagaaccacc agaaccacct cccatcataa 60
tatcgcctac aaat 74

<210> SEQ ID NO 27
<211> LENGTH: 38
<212> TYPE: DNA
<213> ORGANISM: Artificial Sequence
<220> FEATURE:
<223> OTHER INFORMATION: PCR primer

<400> SEQUENCE: 27
cgctggatat ctacatgcac gtatttattg ccattccg 38

-continued

```
<210> SEQ ID NO 28
<211> LENGTH: 74
<212> TYPE: DNA
<213> ORGANISM: Artificial Sequence
<220> FEATURE:
<223> OTHER INFORMATION: PCR primer

<400> SEQUENCE: 28

tacgggatcc accagaacca ccagaaccac cagaaccacc agaaccacct gctacataat     60

ccgaggctct aaag                                                       74


<210> SEQ ID NO 29
<211> LENGTH: 108
<212> TYPE: DNA
<213> ORGANISM: Artificial Sequence
<220> FEATURE:
<223> OTHER INFORMATION: pgsA6

<400> SEQUENCE: 29

cacgtattta ttgccattcc gatcgttttt gtccttatgt tcgctttcat gtgggcggga     60

aaagcggaaa cgccgaaggt caaaacgtat tctgacgacg tactctca                 108


<210> SEQ ID NO 30
<211> LENGTH: 138
<212> TYPE: DNA
<213> ORGANISM: Artificial Sequence
<220> FEATURE:
<223> OTHER INFORMATION: pgsA7

<400> SEQUENCE: 30

cacgtattta ttgccattcc gatcgttttt gtccttatgt tcgctttcat gtgggcggga     60

aaagcggaaa cgccgaaggt caaaacgtat tctgacgacg tactctcagc ctcatttgta    120

ggcgatatta tgatggga                                                  138


<210> SEQ ID NO 31
<211> LENGTH: 228
<212> TYPE: DNA
<213> ORGANISM: Artificial Sequence
<220> FEATURE:
<223> OTHER INFORMATION: pgsA8

<400> SEQUENCE: 31

cacgtattta ttgccattcc gatcgttttt gtccttatgt tcgctttcat gtgggcggga     60

aaagcggaaa cgccgaaggt caaaacgtat tctgacgacg tactctcagc ctcatttgta    120

ggcgatatta tgatgggacg ctatgttgaa aaagtaacgg agcaaaaagg ggcagacagt    180

atttttcaat atgttgaacc gatctttaga gcctcggatt atgtagca                 228
```